United States Patent [19]
Kern et al.

[11] Patent Number: 5,955,292
[45] Date of Patent: Sep. 21, 1999

[54] TUMOR SUPPRESSOR GENE, DPC4

[75] Inventors: Scott E. Kern, Hunt Valley, Md.;
Stephan A. Hahn, Wilten, Germany

[73] Assignee: The Johns Hopkins University School of Medicine, Baltimore, Md.

[21] Appl. No.: 09/005,532

[22] Filed: Jan. 12, 1998

Related U.S. Application Data

[62] Division of application No. 08/588,821, Jan. 19, 1996, Pat. No. 5,712,097.
[51] Int. Cl.$^6$ .................. G01N 33/574; C07K 16/30; C07K 16/32
[52] U.S. Cl. ................ 435/7.23; 436/64; 436/813; 530/387.7; 530/387.9; 530/388.8; 530/389.7
[58] Field of Search ............... 435/7.23; 436/64, 436/813; 530/387.7, 387.9, 388.8, 389.7

[56] References Cited

PUBLICATIONS

Auffray et al., EMBC/GenBank Accession No. F 11191, F 10678, F 13084 (1995).

Stratagene Catalog (1988), p. 39.

*Primary Examiner*—Toni R. Scheiner
*Attorney, Agent, or Firm*—Fish & Richardson P.C.

[57] ABSTRACT

Polynucleotide and polypeptide sequences encoding a novel tumor suppressor gene, DPC4, are provided. Also included is a method for detecting a cell proliferative disorder associated with DPC4. DPC4 is a marker which can be used diagnostically, prognostically and therapeutically over the course of disorders associated with DPC4.

9 Claims, 11 Drawing Sheets

```
  1 GGTTATCCTGAATACATGTCTAACAATTTCCTTGCAACGTTAGCTGTGTTTTCACTGTTTCCAAAGGATCAAAA
 78 TTGCTTCAGAAATTGGAGACATATTTGATTTAAAAGGAAAAACTTGAACAAATGTCTATTACGAATACA
  1                                                      M  S  I  T  N  T
156 CCAACAAGTAATGATGCCTGTCTGAGCATTGTGCATAGTTTGATGTGCCATAGACAAGGTGGAGAGAGTGAAACATTT
 10  P  T  S  N  D  A  C  L  S  I  V  H  S  L  M  C  H  R  Q  G  G  E  S  E  T  F
234 GCAAAAGAGCAATTGAAAGTTTGGTAAGAAGCTGAAGGAGAAAAGATGAATTGGATTCTTAATAACAGCTATA
 36  A  K  R  A  I  E  S  L  V  K  K  L  K  E  K  D  E  L  D  S  L  I  T  A  I
312 ACTACAAATGGAGCTCATCCTAGTAAATGTGTTACCATAGAGAACATTGGATGGGAGGCTTCAGGTGCTGGTCGG
 62  T  T  N  G  A  H  P  S  K  C  V  T  I  Q  R  T  L  D  G  R  L  Q  V  A  G  R
390 AAAGGATTCCTCATGTGATCTTGACTTAAAAATGTGATAGTGTCTGTGTGAATCCATATCACTACGAACGAGTTGTATCACCT
 88  K  G  F  P  H  V  I  Y  A  R  L  W  R  W  P  D  L  H  K  N  E  L  K  H  V  K
468 TATTGTCAGTATGCGTTTGACTTAAAAATGTGATAGTGTCTGTGTGAATCCATATCACTACGAACGAGTTGTATCACCT
114  Y  C  Q  Y  A  F  D  L  K  C  D  S  V  C  V  N  P  Y  H  Y  E  R  V  V  S  P
546 GGAATTGATCTCTCAGGATTAACACTCGTTGTCCACTGAAGGACATTCAAACCATCCAGTATGATGAATATGTGCATGAC
140  G  I  D  L  S  G  L  T  L  Q  S  N  A  P  S  S  M  M  V  K  D  E  Y  V  H  D
624 TTTGAGGGACAGCCATCGTTGTCCACTGAAGGACATTCAAACCATCCAGTATGATGAATATGTGCATGAC
166  F  E  G  Q  P  S  L  S  T  E  G  H  S  I  Q  T  I  Q  H  P  P  S  N  R  A  S
702 ACAGAGACATACAGCTTCCACAAGTCAGCCTGCCAGTATACTGGGGGCAGCCATAGTGAAGGACTGTTGCAGATAGCATCAGG
192  T  E  T  Y  S  T  P  A  L  L  A  P  S  E  S  N  A  T  S  T  A  N  F  P  N  I
780 CCTGTGGCTTCCACAAGTCAGCCTGCCAGTATACTGGGGGCAGCCATAGTGAAGGACTGTTGCAGATAGCATCAGG
218  P  V  A  S  T  S  Q  P  A  S  I  L  G  G  S  H  S  E  G  L  L  Q  I  A  S  G
858 CCTCAGCCAGGACAGCAGCAGCAGAATGGATTTACTGGTCAGCCAGCCACTTACCATCATAACAGCACTACCACCTGGACT
244  P  Q  P  G  Q  Q  Q  Q  N  G  F  T  G  Q  P  A  T  Y  H  H  N  S  T  T  T  W  T
```

FIG. 3A

```
 936 GGAAGTAGGAGGACTGCACCATACACACCTAATTTGCCTCACCACCAAAACGGCCATCTTCAGCACCACCCGCCTATGCCG
 270  G  S  R  R  L  H  H  T  P  N  L  P  H  H  Q  N  G  H  L  Q  H  P  P  M  P

1014 CCCCATCCCGGACATTACTGGCCTGTTCACAATGAGCTTGCATTCCAGCCTCCCATTTCCAATCATCCTGCTCCTGAG
 296  P  H  P  G  H  Y  W  P  V  H  N  E  L  A  F  Q  P  P  I  S  N  H  P  A  P  E

1092 TATTGGTGTGTTCCATTGCTTACTTTGAAATGGATGTTCAGGTAGGAGAGACATTTAAGGTTCCTTCAAGCTGCCCTATT
 322  Y  W  C  S  I  A  Y  F  E  M  D  V  Q  V  G  E  T  F  K  V  P  S  S  C  P  I

1170 GTTACTGTTGATGGATACGTGGACCCTTCTGGAGGAGATCGCTTTTGTTGGGTCAACTCTCCAATGTCCACAGGACA
 348  V  T  V  D  G  Y  V  D  P  S  G  G  D  R  F  C  L  G  Q  L  S  N  V  H  R  T

1248 GAAGCCAATTGAGAGAGCAAGGTTGCACATAGGCAAAGGTGTGCAGTTGGAATGTAAAGGTGAAGGTGATGTTTGGGTC
 374  E  A  I  E  R  A  R  L  H  I  G  K  G  V  Q  L  E  C  K  G  E  G  D  V  W  V

1326 AGGTGCCTTAGTGACCACGCGGTCTTTGTACAGAGTTACTACTTAGACAGAGAAGCTGGCCGTGCACCTGGAGATGCT
 400  R  C  L  S  D  H  A  V  F  V  Q  S  Y  Y  L  D  R  E  A  G  R  A  P  G  D  A

1404 GTTCATAAGATCTACCCAAGTGCATATATAAAGGTCTTTGATTTGCGTCAGTGTCATCGACAGCATCGACAGCAGCCG
 426  V  H  K  I  Y  P  S  A  Y  I  K  V  F  D  L  R  Q  C  H  R  Q  M  Q  Q  Q  A

1482 GCTACTGCACAAGCTGCAGCAGCTGCCGTGGCCAGGAAACATCCCTGGCCAGGATCAGTAGGTGGA
 452  A  T  A  Q  A  A  A  A  V  A  G  N  I  P  G  P  G  S  V  G  G

1560 ATAGCTCCAGCTATCAGTCTGTGGGACCGGATTACCCAAGACAGAGCATCAAAGAAACACCTTGCTGGATTGAAATTCACTTA
 478  I  A  P  A  I  S  L  S  A  A  A  G  I  G  V  D  D  L  R  R  L  C  I  L  R  M

1638 AGTTTTGTGAAAGGCTGGGGACCGGATTACCCAAGACAGAGCATCAAAGAAACACCTTGCTGGATTGAAATTCACTTA
 504  S  F  V  K  G  W  G  P  D  Y  P  R  Q  S  I  K  E  T  P  C  W  I  E  I  H  L

1716 CACCGGGCCCTCCAGCTCCTAGACGAAGTACTTCATAGACGAAGTACTTCATACCATGCCGATTGCAGACCCACAACCTTTAGACTGAGGTCTT
```

1794 TTACCGTTGGGCCCTTAACCTTATCAGGATGGTGGACTACAAATACAATCCTGTTTATAATCTGAAGATATATTC
1872 ACTTTTCTTCTGCTTTATCTTTTCATAAAGGGTTGAAAATGTGTTTGCTGCCTTGCTCCTAGCAGACAGAAACTGGAT
1950 TAAAACAATTTTTTTTCCCTCTTCAGAACTTGTCAGGCATGGCTCAGAGCTTGAAGATTAGGAGAAACACATTCTTAT
2028 TAATTCTTCACCTGTTATGTATGAAGGAATCATTCCAGTGCTAGAAAATTTAGCCCTTTAAAACGTCTTAGAGCCTTT
2106 TATCTGCAGAACATCGATATGTATATCATTCTACAGAATAATCCAGTATTGCTGATTTTAAAGGCAGAGAAGTTCTCA
2184 AAGTTAATTCACCTATGTTATTTTGTGTACAAGTTGTTATTGTTGAACATACTTCAAAATAAATGTATTGTAATCTTTCATCCAAAAT
2262 AGTTAATTTTACCAAGAGTAACTTTACTCTGTGTTTAAAATGAAGTTAATAATGTATTGTAATCTTCAGTTTTATTTTTGCCAAGGCA
2340 ATTTTTTGCAAGTTATATTAGTGAAGATGGTTTCAATTCAGATTGTCTTGCAACTTCAGTTTTATTTTTGCCAAGGCA
2418 AAAAACTCTTAATCTGTGTGTATATTGAGAAGTATACTTTTCCCCTGTTAAACAGTAGTTGTATTCTTCTGTATTCTAGGCACAA
2496 CCTAGTGGATGACTGTTGATGAAGCCTATAAGAGGAATTTCTTTTCCTTCATTCATAGGGAAAGGTTTTGTATTTTTAAAACAC
2574 GGTTGGTTGCTAAGAAGCCTATAAGAGGAATTTCTTTTCCTTCATTCATAGGGAAAGGTTTTGTATTTTTAAAACAC
2652 TAAAAGCAGCGTCACTCTACCTAATGTCT

FIG. 3C

```
DPC4   27  KOGGESETEARRAIESLVKKLKEKKDELDSLITAITTNGAHESKCVTIQRSLDGRLOV
sma2   17  KOGDEDEKWAKKAIDNLVKKL---KQALENLEFALRCQGQQKIECVTIPRSLDGRLQ
Mad    35  KOGDEEKWAERAVDSLVKKLKKRKGAIEELERALSCPGQ-ESKCVTIPRSLDGRLQV DPC4   85  AGRKGFPHVIYARLWRWPDLHKNELKHVKYCQYAFDLKCDSVCVNPYHYKRVVSPG
sma2   92  SHRKAIPHVIYCRVTRWPDL--HELKAIEDCRFCYESGQKDICINPYHYKRVHITC
Mad    76  SHRKGLPHVIYCRVWRWPDL--HELKPLELCQYPFSARQKEVCINPYHYKRVESPVL DPC4  316  NHPAPEYWCSIAYFEMDVCGETKVPSSCPIVTVDGYVDPSGGDRFC
sma2  215  KVWEEQFWATVSYYELNTRVGEQVKVSST---IEIDGFIDPCINGSKI
Mad   254  SYSEFAFWASIAYYELNCRVGEVEHCNNNS--VIVDGFTNPSNNSDRC DPC4  357  SCGDRFCLGQLSNVHRTEAIERARLHIGKGVQLECKGEGDVWVRCLSDHAVFVQS
sma2  255  INCSKISLGLFSNVNRNATIENTRRHIGNGVKL--RSNGSLFACCESDSARFVQS
Mad   294  NNSDRCCLGQLSNVNRNSTIENTRFHIGKGVHL-----GEYAECLSDSADFVQS DPC4  492  VDDLRRLCILRMSFVKGWGPDYPRQSIKETPCWIEIHLHRALLLDEVHTW
sma2  356  SFDLQKMTFIRMSFVKGWGAEYQRQDVTSTPCWIEIHLHAPLAWLDRVLSTM
Mad   393  VYELTKMCTIRMSFVKGWGAEYHRQDVTSTPCWIEIHLHGPLWLDKVLTQM
```

FIG. 4

SEQUENCE LISTING (1) GENERAL INFORMATION:

(iii) NUMBER OF SEQUENCES: 91

(2) INFORMATION FOR SEQ ID NO:1:

(i) SEQUENCE CHARACTERISTICS:
        (A) LENGTH: 2680 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:1:

```
GGTTATCCTG AATACATGTC TAACAATTTT CCTTGCAACG TTAGCTGTTG TTTTTCACTG      60

TTTCCAAAGG ATCAAAATTG CTTCAGAAAT TGGAGACATA TTTGATTTAA AAGGAAAAAC     120

TTGAACAAAT GGACAATATG TCTATTACGA ATACACCAAC AAGTAATGAT GCCTGTCTGA     180

GCATTGTGCA TAGTTTGATG TGCCATAGAC AAGGTGGAGA GAGTGAAACA TTTGCAAAAA     240

GAGCAATTGA AAGTTTGGTA AAGAAGCTGA AGGAGAAAAA AGATGAATTG GATTCTTTAA     300

TAACAGCTAT AACTACAAAT GGAGCTCATC CTAGTAAATG TGTTACCATA CAGAGAACAT     360

TGGATGGGAG GCTTCAGGTG GCTGGTCGGA AAGGATTTCC TCATGTGATC TATGCCCGTC     420

TCTGGAGGTG GCCTGATCTT CACAAAAATG AACTAAAACA TGTTAAATAT TGTCAGTATG     480

CGTTTGACTT AAAATGTGAT AGTGTCTGTG TGAATCCATA TCACTACGAA CGAGTTGTAT     540

CACCTGGAAT TGATCTCTCA GGATTAACAC TGCAGAGTAA TGCTCCATCA AGTATGATGG     600

TGAAGGATGA ATATGTGCAT GACTTTGAGG GACAGCCATC GTTGTCCACT GAAGGACATT     660

CAATTCAAAC CATCCAGCAT CCACCAAGTA ATCGTGCATC GACAGAGACA TACAGCACCC     720

CAGCTCTGTT AGCCCCATCT GAGTCTAATG CTACCAGCAC TGCCAACTTT CCCAACATTC     780

CTGTGGCTTC CACAAGTCAG CCTGCCAGTA TACTGGGGGG CAGCCATAGT GAAGGACTGT     840

TGCAGATAGC ATCAGGGCCT CAGCCAGGAC AGCAGCAGAA TGGATTTACT GGTCAGCCAG     900

CTACTTACCA TCATAACAGC ACTACCACCT GGACTGGAAG TAGGACTGCA CCATACACAC     960

CTAATTTGCC TCACCACCAA AACGGCCATC TTCAGCACCA CCCGCCTATG CCGCCCCATC    1020

CCGGACATTA CTGGCCTGTT CACAATGAGC TTGCATTCCA GCCTCCCATT TCCAATCATC    1080

CTGCTCCTGA GTATTGGTGT TCCATTGCTT ACTTTGAAAT GGATGTTCAG GTAGGAGAGA    1140

CATTTAAGGT TCCTTCAAGC TGCCCTATTG TTACTGTTGA TGGATACGTG GACCCTTCTG    1200

GAGGAGATCG CTTTTGTTTG GGTCAACTCT CCAATGTCCA CAGGACAGAA GCCATTGAGA    1260

GAGCAAGGTT GCACATAGGC AAAGGTGTGC AGTTGGAATG TAAAGGTGAA GGTGATGTTT    1320

GGGTCAGGTG CCTTAGTGAC CACGCGGTCT TTGTACAGAG TTACTACTTA GACAGAGAAG    1380

CTGGGCGTGC ACCTGGAGAT GCTGTTCATA AGATCTACCC AAGTGCATAT ATAAAGGTCT    1440

TTGATTTGCG TCAGTGTCAT CGACAGATGC AGCAGCAGGC GGCTACTGCA CAAGCTGCAG    1500

CAGCTGCCCA GGCAGCAGCC GTGGCAGGAA ACATCCCTGG CCCAGGATCA GTAGGTGGAA    1560

TAGCTCCAGC TATCAGTCTG TCAGCTGCTG CTGGAATTGG TGTTGATGAC CTTCGTCGCT    1620
```

```
TATGCATACT CAGGATGAGT TTTGTGAAAG GCTGGGGACC GGATTACCCA AGACAGAGCA    1680

TCAAAGAAAC ACCTTGCTGG ATTGAAATTC ACTTACACCG GGCCCTCCAG CTCCTAGACG    1740

AAGTACTTCA TACCATGCCG ATTGCAGACC CACAACCTTT AGACTGAGGT CTTTTACCGT    1800

TGGGGCCCTT AACCTTATCA GGATGGTGGA CTACAAAATA CAATCCTGTT TATAATCTGA    1860

AGATATATTT CACTTTTCTT CTGCTTTATC TTTTCATAAA GGGTTGAAAA TGTGTTTGCT    1920

GCCTTGCTCC TAGCAGACAG AAACTGGATT AAAACAATTT TTTTTTCCTC TTCAGAACTT    1980

GTCAGGCATG GCTCAGAGCT TGAAGATTAG GAGAAACACA TTCTTATTAA TTCTTCACCT    2040

GTTATGTATG AAGGAATCAT TCCAGTGCTA GAAAATTTAG CCCTTTAAAA CGTCTTAGAG    2100

CCTTTTATCT GCAGAACATC GATATGTATA TCATTCTACA GAATAATCCA GTATTGCTGA    2160

TTTTAAAGGC AGAGAAGTTC TCAAAGTTAA TTCACCTATG TTATTTTGTG TACAAGTTGT    2220

TATTGTTGAA CATACTTCAA AAATAATGTG CCATGTGGGT GAGTTAATTT TACCAAGAGT    2280

AACTTTACTC TGTGTTTAAA AATGAAGTTA ATAATGTATT GTAATCTTTC ATCCAAAATA    2340

TTTTTTGCAA GTTATATTAG TGAAGATGGT TTCAATTCAG ATTGTCTTGC AACTTCAGTT    2400

TTATTTTTGC CAAGGCAAAA AACTCTTAAT CTGTGTGTAT ATTGAGAATC CCTTAAAATT    2460

ACCAGACAAA AAAATTTAAA ATTACGTTTG TTATTCCTAG TGGATGACTG TTGATGAAGT    2520

ATACTTTTCC CCTGTTAAAC AGTAGTTGTA TTCTTCTGTA TTTCTAGGCA CAAGGTTGGT    2580

TGCTAAGAAG CCTATAAGAG GAATTTCTTT TCCTTCATTC ATAGGGAAAG GTTTTGTATT    2640

TTTTAAAACA CTAAAAGCAG CGTCACTCTA CCTAATGTCT                          2680
```

(2) INFORMATION FOR SEQ ID NO:2:

(i) SEQUENCE CHARACTERISTICS:
        (A) LENGTH: 552 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asp Asn Met Ser Ile Thr Asn Thr Pro Thr Ser Asn Asp Ala Cys
  1               5                  10                  15

Leu Ser Ile Val His Ser Leu Met Cys His Arg Gln Gly Gly Glu Ser
             20                  25                  30

Glu Thr Phe Ala Lys Arg Ala Ile Glu Ser Leu Val Lys Lys Leu Lys
         35                  40                  45

Glu Lys Lys Asp Glu Leu Asp Ser Leu Ile Thr Ala Ile Thr Thr Asn
     50                  55                  60

Gly Ala His Pro Ser Lys Cys Val Thr Ile Gln Arg Thr Leu Asp Gly
 65                  70                  75                  80

Arg Leu Gln Val Ala Gly Arg Lys Gly Phe Pro His Val Ile Tyr Ala
                 85                  90                  95

Arg Leu Trp Arg Trp Pro Asp Leu His Lys Asn Glu Leu Lys His Val
            100                 105                 110

Lys Tyr Cys Gln Tyr Ala Phe Asp Leu Lys Cys Asp Ser Val Cys Val
        115                 120                 125

Asn Pro Tyr His Tyr Glu Arg Val Val Ser Pro Gly Ile Asp Leu Ser
    130                 135                 140

Gly Leu Thr Leu Gln Ser Asn Ala Pro Ser Ser Met Met Val Lys Asp
145                 150                 155                 160

Glu Tyr Val His Asp Phe Glu Gly Gln Pro Ser Leu Ser Thr Glu Gly
```

```
                        165                 170                 175
His Ser Ile Gln Thr Ile Gln His Pro Pro Ser Asn Arg Ala Ser Thr
                    180                 185                 190
Glu Thr Tyr Ser Thr Pro Ala Leu Leu Ala Pro Ser Glu Ser Asn Ala
                195                 200                 205
Thr Ser Thr Ala Asn Phe Pro Asn Ile Pro Val Ala Ser Thr Ser Gln
            210                 215                 220
Pro Ala Ser Ile Leu Gly Gly Ser His Ser Glu Gly Leu Leu Gln Ile
225                 230                 235                 240
Ala Ser Gly Pro Gln Pro Gly Gln Gln Asn Gly Phe Thr Gly Gln
                245                 250                 255
Pro Ala Thr Tyr His His Asn Ser Thr Thr Thr Trp Thr Gly Ser Arg
                260                 265                 270
Thr Ala Pro Tyr Thr Pro Asn Leu Pro His His Gln Asn Gly His Leu
            275                 280                 285
Gln His His Pro Pro Met Pro Pro His Pro Gly His Tyr Trp Pro Val
        290                 295                 300
His Asn Glu Leu Ala Phe Gln Pro Pro Ile Ser Asn His Pro Ala Pro
305                 310                 315                 320
Glu Tyr Trp Cys Ser Ile Ala Tyr Phe Glu Met Asp Val Gln Val Gly
                325                 330                 335
Glu Thr Phe Lys Val Pro Ser Ser Cys Pro Ile Val Thr Val Asp Gly
                340                 345                 350
Tyr Val Asp Pro Ser Gly Gly Asp Arg Phe Cys Leu Gly Gln Leu Ser
            355                 360                 365
Asn Val His Arg Thr Glu Ala Ile Glu Arg Ala Arg Leu His Ile Gly
        370                 375                 380
Lys Gly Val Gln Leu Glu Cys Lys Gly Glu Gly Asp Val Trp Val Arg
385                 390                 395                 400
Cys Leu Ser Asp His Ala Val Phe Val Gln Ser Tyr Tyr Leu Asp Arg
                405                 410                 415
Glu Ala Gly Arg Ala Pro Gly Asp Ala Val His Lys Ile Tyr Pro Ser
                420                 425                 430
Ala Tyr Ile Lys Val Phe Asp Leu Arg Gln Cys His Arg Gln Met Gln
            435                 440                 445
Gln Gln Ala Ala Thr Ala Gln Ala Ala Ala Gln Ala Ala
        450                 455                 460
Val Ala Gly Asn Ile Pro Gly Pro Gly Ser Val Gly Gly Ile Ala Pro
465                 470                 475                 480
Ala Ile Ser Leu Ser Ala Ala Gly Ile Gly Val Asp Asp Leu Arg
                485                 490                 495
Arg Leu Cys Ile Leu Arg Met Ser Phe Val Lys Gly Trp Gly Pro Asp
            500                 505                 510
Tyr Pro Arg Gln Ser Ile Lys Glu Thr Pro Cys Trp Ile Glu Ile His
        515                 520                 525
Leu His Arg Ala Leu Gln Leu Leu Asp Glu Val Leu His Thr Met Pro
    530                 535                 540
Ile Ala Asp Pro Gln Pro Leu Asp
545                 550

(2) INFORMATION FOR SEQ ID NO:3:

(i) SEQUENCE CHARACTERISTICS:
        (A) LENGTH: 60 base pairs
        (B) TYPE: nucleic acid
```

(C) STRANDEDNESS: single
(D) TOPOLOGY: linear (ii) MOLECULE TYPE: DNA (xi) SEQUENCE DESCRIPTION: SEQ ID NO:3:

GGATCCTAAT ACGACTCACT ATAGGGCCGC CACCATGGCC TGTCTGAGCA TTGTGCATAG      60

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

CAGTTTCTGT CTGCTAGGAG      20

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

CGTTAGCTGT TGTTTTTCAC TG      22

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

AGAGTATGTG AAGAGATGGA G      21

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

TGTATGACAT GGCCAAGTTA G      21

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

CAATACTCGG TTTTAGCAGT C                                                    21

(2) INFORMATION FOR SEQ ID NO:9:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:9:

TTTAAAGTAA CTATCTGACT ATAC                                                 24

(2) INFORMATION FOR SEQ ID NO:10:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:10:

GCCCCTAACC TCAAAATCTA C                                                    21

(2) INFORMATION FOR SEQ ID NO:11:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:11:

TTTTGCTGGT AAAGTAGTAT GC                                                   22

(2) INFORMATION FOR SEQ ID NO:12:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:12:

CTATGAAAGA TAGTACAGTT AC                                                   22

(2) INFORMATION FOR SEQ ID NO:13:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:13:

CATCTTTATA GTTGTGCATT ATC                                                  23

(2) INFORMATION FOR SEQ ID NO:14:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

TAATGAAACA AAATCACAGG ATG                      23

(2) INFORMATION FOR SEQ ID NO:15:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

TGAAAGTTTT AGCATTAGAC AAC                      23

(2) INFORMATION FOR SEQ ID NO:16:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

TGTACTCATC TGAGAAGTGA C                        21

(2) INFORMATION FOR SEQ ID NO:17:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

TGTTTTGGGT GCATTACATT TC                       22

(2) INFORMATION FOR SEQ ID NO:18:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

CAATTTTTTA AAGTAACTAT CTGA                     24

(2) INFORMATION FOR SEQ ID NO:19:

(i) SEQUENCE CHARACTERISTICS:
        (A) LENGTH: 22 base pairs
        (B) TYPE: nucleic acid (C) STRANDEDNESS: single
        (D) TOPOLOGY: linear (ii) MOLECULE TYPE: DNA (xi) SEQUENCE DESCRIPTION: SEQ ID NO:19:

TATTAGCATG CTATACAATC TG                    22

(2) INFORMATION FOR SEQ ID NO:20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

CTTCCACCCA GATTTCAATT C                     21

(2) INFORMATION FOR SEQ ID NO:21:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

AGGCATTGGT TTTAATGTAT G                     21

(2) INFORMATION FOR SEQ ID NO:22:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

CTGCTCAAAG AAACTAATCA AC                    22

(2) INFORMATION FOR SEQ ID NO:23:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:23:

CCAAAAGTGT GCAGCTTGTT G                     21

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA -continued (xi) SEQUENCE DESCRIPTION: SEQ ID NO:24:

CAGTTTCTGT CTGCTAGGAG                                           20

(2) INFORMATION FOR SEQ ID NO:25:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:25:

TTTCCAAAGG ATCAAAATTG CTTGCTTCAG                                30

(2) INFORMATION FOR SEQ ID NO:26:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:26:

TAATACTGAG TTGGTAGGAT TGTGAG                                    26

(2) INFORMATION FOR SEQ ID NO:27:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:27:

CTCACACAAA CTAATTCTAG GTCAAC                                    26

(2) INFORMATION FOR SEQ ID NO:28:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:28:

GGAGTTTCCC CCCAAGTGAC TAC                                       23

(2) INFORMATION FOR SEQ ID NO:29:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:29:

TGAAATCATA AGATGACATC TATGAATG                                  28

(2) INFORMATION FOR SEQ ID NO:30:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:30:

CTGGACTGGA AGTAGGACTG                                           20

(2) INFORMATION FOR SEQ ID NO:31:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:31:

TCCGGGATGG GGCGGCATAG                                           20

(2) INFORMATION FOR SEQ ID NO:32:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:32:

CACTAAATCA ATCTAAATAC AGGAAATC                                  28

(2) INFORMATION FOR SEQ ID NO:33:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:33:

TGTGTTGTGG AGTGCAAGTG AAAG                                      24

(2) INFORMATION FOR SEQ ID NO:34:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:34:

TTTTGACAAC AAATAGAGCT TTAAGTC                                   27

(2) INFORMATION FOR SEQ ID NO:35:

(i) SEQUENCE CHARACTERISTICS:
        (A) LENGTH: 23 base pairs
        (B) TYPE: nucleic acid (C) STRANDEDNESS: single
        (D) TOPOLOGY: linear (ii) MOLECULE TYPE: DNA (xi) SEQUENCE DESCRIPTION: SEQ ID NO:35:

GAATTTTCTT TATGAACTCA TAG                                              23

(2) INFORMATION FOR SEQ ID NO:36:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:36:

TATTTTGTAG TCCACCATC                                                   19

(2) INFORMATION FOR SEQ ID NO:37:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:37:

CAGAGCTCC                                                               9

(2) INFORMATION FOR SEQ ID NO:38:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:38:

GAGAATAGAA GGATGGTGAC                                                  20

(2) INFORMATION FOR SEQ ID NO:39:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:39:

AATTGACAGG CAGCAAGTAG                                                  20

(2) INFORMATION FOR SEQ ID NO:40:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:40:

AATTGACAGG CAGCAAGTAG                 20

(2) INFORMATION FOR SEQ ID NO:41:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:41:

ATGTGTACCC AGAAGGAAAG                 20

(2) INFORMATION FOR SEQ ID NO:42:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:42:

GCACATTTGG ATTCTATCTA G                 21

(2) INFORMATION FOR SEQ ID NO:43:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:43:

CTCCTTGCCT TAAAGAATCA G                 21

(2) INFORMATION FOR SEQ ID NO:44:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:44:

AGGGCCTGGC AGTATGAAAG                 20

(2) INFORMATION FOR SEQ ID NO:45:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:45:

ATGCAGGCCC TTCACAGAC                 19

(2) INFORMATION FOR SEQ ID NO:46:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:46:

ATTGGTTTCT CCAGAGTTTT G                                      21

(2) INFORMATION FOR SEQ ID NO:47:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:47:

TTGTTCCTCT CTCATGATTT G                                      21

(2) INFORMATION FOR SEQ ID NO:48:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:48:

AATATGGTGG TTTAAAGACA TG                                    22

(2) INFORMATION FOR SEQ ID NO:49:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:49:

GTGCATAATG CCGAATGTTC                                        20

(2) INFORMATION FOR SEQ ID NO:50:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:50:

CATCTCATTT GAATTTGAGA AAG                                  23

(2) INFORMATION FOR SEQ ID NO:51:

(i) SEQUENCE CHARACTERISTICS:
        (A) LENGTH: 23 base pairs
        (B) TYPE: nucleic acid

```
        (C) STRANDEDNESS: single
        (D) TOPOLOGY: linear (ii) MOLECULE TYPE: DNA (xi) SEQUENCE DESCRIPTION: SEQ ID NO:51:

TAAGATCTTT TCATTGGATT ATG                                              23

(2) INFORMATION FOR SEQ ID NO:52:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:52:

AAATCAGTTG TATTTCTATT CAC                                              23

(2) INFORMATION FOR SEQ ID NO:53:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:53:

TCTTGACTTT TTCAGAAGTG TTG                                              23

(2) INFORMATION FOR SEQ ID NO:54:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:54:

GTGGTCTGGA GAGTCTAAAC                                                  20

(2) INFORMATION FOR SEQ ID NO:55:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:55:

TACCTTGGCT GCCAAACATC                                                  20

(2) INFORMATION FOR SEQ ID NO:56:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA
```

(xi) SEQUENCE DESCRIPTION: SEQ ID NO:56:

ATGGGCTTAT AACTGTGATA G                     21

(2) INFORMATION FOR SEQ ID NO:57:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:57:

CTTACAACAA TGCTAGTAAG A                     21

(2) INFORMATION FOR SEQ ID NO:58:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:58:

TCCCCTTCAC AGCTAGCAAG                       20

(2) INFORMATION FOR SEQ ID NO:59:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:59:

TCATTTTCGC ACAGGCAAAC                       20

(2) INFORMATION FOR SEQ ID NO:60:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:60:

GCTTTGTAAC TTGCTTTGAT TC                    22

(2) INFORMATION FOR SEQ ID NO:61:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:61:

CTGGCTAAAC TTCCCAAATG                       20

(2) INFORMATION FOR SEQ ID NO:62:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:62:

CTGCAGCTCT GTGAGATG                                    18

(2) INFORMATION FOR SEQ ID NO:63:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:63:

TTATACCAAT TATGGGAAAC AG                            22

(2) INFORMATION FOR SEQ ID NO:64:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:64:

TTATACCAAT TATGGGAAAC AG                            22

(2) INFORMATION FOR SEQ ID NO:65:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:65:

AATTAAAATT CACAACAATA GTG                          23

(2) INFORMATION FOR SEQ ID NO:66:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:66:

CCCTGCAACA CACAATTTAC                                20

(2) INFORMATION FOR SEQ ID NO:67:

(i) SEQUENCE CHARACTERISTICS:
        (A) LENGTH: 20 base pairs
        (B) TYPE: nucleic acid (C) STRANDEDNESS: single
        (D) TOPOLOGY: linear (ii) MOLECULE TYPE: DNA (xi) SEQUENCE DESCRIPTION: SEQ ID NO:67:

GAGGGCAGGA AAGGAAATAC                                                      20

(2) INFORMATION FOR SEQ ID NO:68:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:68:

CCGTACCTGG CCAGAAGTC                                                       19

(2) INFORMATION FOR SEQ ID NO:69:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:69:

ATGACATGAT GGTGATGATT TG                                                   22

(2) INFORMATION FOR SEQ ID NO:70:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:70:

TCCCAAAGTG CTGGGATTTC                                                      20

(2) INFORMATION FOR SEQ ID NO:71:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:71:

GTGAGTTGCT GGGATTAGAG                                                      20

(2) INFORMATION FOR SEQ ID NO:72:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:72:

GTTCTGCAGT GAAATTGGTG                                        20

(2) INFORMATION FOR SEQ ID NO:73:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:73:

ACAGCAGTTT GGGACAAGTG                                        20

(2) INFORMATION FOR SEQ ID NO:74:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:74:

GTCCACGTAT CCATCAACAG                                        20

(2) INFORMATION FOR SEQ ID NO:75:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:75:

CTTACTTTGA AATGGATGTT CAG                                    23

(2) INFORMATION FOR SEQ ID NO:76:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:76:

TGAACTAATA GCCAAGAACT                                        20

(2) INFORMATION FOR SEQ ID NO:77:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:77:

AATCTACCTT GCTAGGAAT                                         19

(2) INFORMATION FOR SEQ ID NO:78:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:78:

TGGGGTGTTT ACCAGCATC                                             19

(2) INFORMATION FOR SEQ ID NO:79:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:79:

TGGCTTTCAA TGTCAGAAGG                                          20

(2) INFORMATION FOR SEQ ID NO:80:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:80:

GAATAGCAGG ACCTATCAAA GAGC                                  24

(2) INFORMATION FOR SEQ ID NO:81:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:81:

CAGATTAAGT GAAAACAGCA TATGTG                               26

(2) INFORMATION FOR SEQ ID NO:82:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:82:

GCTTCATTCT CTCACTGGAT                                          20

(2) INFORMATION FOR SEQ ID NO:83:

(i) SEQUENCE CHARACTERISTICS:
        (A) LENGTH: 20 base pairs
        (B) TYPE: nucleic acid (C) STRANDEDNESS: single
            (D) TOPOLOGY: linear (ii) MOLECULE TYPE: DNA (xi) SEQUENCE DESCRIPTION: SEQ ID NO:83:

TTGGGAACTG CTCTACATTC                                                    20

(2) INFORMATION FOR SEQ ID NO:84:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:84:

AATGCCCAGC AGAGTG                                                        16

(2) INFORMATION FOR SEQ ID NO:85:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:85:

AGTGGTTTGA CAGAGAGTGC                                                    20

(2) INFORMATION FOR SEQ ID NO:86:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:86:

TGTCTGAGCA TTGTGCATAG                                                    20

(2) INFORMATION FOR SEQ ID NO:87:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:87:

AAGCCTCCCA TCCAATGTTC                                                    20

(2) INFORMATION FOR SEQ ID NO:88:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA

```
       (xi) SEQUENCE DESCRIPTION: SEQ ID NO:88:

AGAAACACCT TGCTGGATTG                                                   20

(2) INFORMATION FOR SEQ ID NO:89:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO:89:

CAGTTTCTGT CTGCTAGGAG                                                   20

(2) INFORMATION FOR SEQ ID NO:90:

(i) SEQUENCE CHARACTERISTICS:
           (A) LENGTH: 21 base pairs
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO:90:

ATACATGGCT TTCCTGGGCA G                                                 21

(2) INFORMATION FOR SEQ ID NO:91:

(i) SEQUENCE CHARACTERISTICS:
           (A) LENGTH: 21 base pairs
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO:91:

CCTCCGCTGT GACGGTGTCC A                                                 21
```

TUMOR SUPPRESSOR GENE, DPC4

This a divisional of U.S. application Ser. No. 08/588,821, filed Jan. 19, 1996, now U.S. Pat. No. 5,712,097.

This invention was made with support from Grant Number CA 62924, awarded by the National Institute of Health. The government has certain rights in the invention.

BACKGROUND OF THE INVENTION

1. Field of the Invention

This invention relates generally to gene expression in normal and neoplastic cells, and specifically to a novel tumor suppressor gene, DPC4.

2. Description of Related Art

The development of human cancer involves the clonal evolution of cell populations which gain competitive advantages over other cells through the alteration of at least two distinct classes of genes: proto-oncogenes and tumor suppressor genes (Weinberg, R. A., Science, 254:1138, 1991; Bishop, J. M., Science, 235:305, 1987). Tumor suppressor genes are characterized by alterations which inactivate both original alleles (Knudson, J. A. G., Cancer Res., 45:1437, 1985). Many tumor suppressor genes are inactivated by intragenic mutations in one allele accompanied by the loss of a relatively large chromosomal region containing the other gene copy. This loss of one copy of a region or a gene is also called allelic loss or loss of heterozygosity (LOH). The finding of a homozygous deletion within a region suffering a high frequency of LOH, has been crucial to the discovery of several tumor suppressor genes (Dryja, et al., Proc. Natl. Acad. Sci. USA, 83:7391, 1986; Fearon, E. R., et al., Science, 247:49, 1990; Kamb, et al., Science, 264:436, 1994) due to the relatively small sizes of the homozygous deletions.

Genetically, the absence of a gene or its function can occur through biallelic inactivation (Knudson, et al., Cancer Res., 45:1437, 1985). One mode of biallelic inactivation involves the combination of an intragenic mutation of one allele together with the loss of a relatively large chromosomal region containing the second allele (LOH). A second mechanism for biallelic inactivation is a combination of two inactivating point mutations targeting a specific gene. A third involves homozygous deletions. Homozygous deletions are thought to be the result of two steps, the loss of a larger chromosomal region and the separate loss of a considerably smaller area.

Knowledge regarding the frequency of homozygous deletions is very limited. They are generally small regions of a chromosome, and probably most deletions are smaller than 2 Mb in size. Two techniques are available for direct searches of homozygous deletions. One technique is the mapping of a preselected chromosomal area with markers. The dramatic increase of the number of sequence tagged sites(STSs) assigned to individual human chromosomes in recent years makes this approach increasingly productive. Examples for the successful application of this technique are the discovery of genes such as RB1, DCC and MTS1 (Kamb, et al., supra; Dryja, et al., supra; Fearon, E. R., et al., supra). A more elegant way to detect homozygous deletions, without the prior limitation of a preselected chromosomal region is the technique of representational difference analysis (RDA) (Lisitsyn, et al., Science, 259:946, 1993). A number of candidate loci have been identified to date by RDA, including one within the region of the BRCA2 gene (Schutte, et al., Proc. Natl. Acad. Sci., USA, 92:5950, 1995; Lisitsyn, et al., Proc. Natl. Acad. Sci., USA, 92:151, 1995).

The molecular events known in pancreatic ductal tumorigenesis include the acquisition of K-ras mutations in over 80% (Almoguerra, et al., Cell 53:549, 1988; Hruban, et al., Am. J Pathol, 143:545, 1993; Redston, et al., Cancer Res., 54:3025, 1994), mutations of the p53 gene in 50–70% (Redston, et al., supra; Pellegata, et al., Cancer Res., 54:1556, 1994), and mutations or homozygous deletions of the p16 gene in over 85% (Caldas, et al., Nat. Genet., 8:27, 1994). Allelotype data suggested the existence of additional tumor suppressor genes at other loci (Hahn, et al., Cancer Res., 55:4670, 1995; Seymour, et al., Cancer Res., 54:2761, 1994). One such interesting location is chromosome 18q, lost in nearly 90% of pancreatic cancers (Hahn, et al., supra; Seymour, et al., supra; Griffin, et al., Cancer Res., 55:2394, 1995). A candidate suppressor gene, DCC, is included in the involved region of 18q LOH, but due to the length and complexity of the gene (29 exons spanning 1.4 megabases), sequence analyses have not been performed in pancreatic carcinomas nor many other tumor types (Cho, et al., Genomics, 19:525, 1994).

Chronic ulcerative colitis (UC) and Crohn disease (CD) are associated with an increase risk of colorectal neoplasia. In most studies, the spectrum and frequencies of genetic alterations in these neoplasms have not been distinctly different from those seen in sporadic colorectal adenomas and carcinomas. Thus, K-ras mutations, 17p deletions and p53 mutations, 18q deletions and APC mutations have been identified at significant rates (Kern, et al., Gastroenterol, 107:420, 1994; Redston, et al., Gastroenterol., 108:383, 1995; Burmer, et al., Gastroenterol., 99:416, 1990; Meltzer, et al., Cancer Res., 50:3627, 1990; Bell, et al., Br J Cancer, 64:174, 1991; Chen, et al., Gastroenterol., 102:1983, 1992; Burmer, et al., Gastroenterol., 103:1602, 1992; Yin, et al., Gastroenterol., 104:1633, 1993). One candidate gene on 18q is the DCC gene, but DCC, as discussed above, is among the largest genes known and mutational analyses have been difficult (Fearon, et al., supra). Thus the target gene for 18q deletions in colitis-associated neoplasia has remained unknown.

Currently, there is one example of a potential therapeutic target which is localized to a hotspot of homozygous deletions at the p16 gene locus. This deletion at 9p21, found in various tumor types, often includes the MTAP (methylthioadenosine phosphorylase) gene (Olopade, et al., Proc. Natl. Acad. Sci., USA, 92:6489, 1995). The 9p21 region is homozygously deleted in 40% of pancreatic cancers (Caldas, et al., Nature Genet., 8:27, 1994), and half of these deletions include the MTAP gene. This purine salvage pathway member is therefore part of the biochemical difference of certain tumor types and represents a target for a chemotherapeutic intervention. This is an example of how the selective absence of a functional copy of a gene contained within a homozygous deletion in cancer might provide a more specific approach to chemotherapy by potentially facilitating the development of drugs toxic to the tumor cell while remaining non-toxic to normal cells. In the case of pancreatic cancer, the frequent homozygous deletions of 9p21 and 18q provide large regions in which to search for potential tumor-specific therapeutic targets.

SUMMARY OF THE INVENTION

The present invention is based on the discovery of a novel tumor suppressor gene on chromosome 18q, which is inactivated in several tumor types. This gene, called DPC4, for deleted in pancreatic carcinoma, locus 4, is highly conserved and may play a critical role in TGF-β-like signaling pathways in tumor cells.

In a first aspect, the invention provides a substantially pure DCP4 polypeptide and a polynucleotide encoding DPC4. The preferred polypeptide is illustrated in FIG. 3 and SEQ ID NO:2.

In another aspect, the invention provides a method for detecting a cell proliferative or developmental disorder associated with DPC4 in a subject, comprising contacting a target cellular component containing DPC4 with a reagent which detects DPC4 and detecting DPC4. A disorder associated with DPC4 is detectable by analyzing DPC4 protein or nucleic acid. For example, a truncated DPC4 protein, or a homozygous deletion of or intragenic mutation in DPC4 nucleic acid is indicative of such a disorder.

Further, the invention provides a method of treating a cell proliferative disorder associated with DPC4, comprising administering to a subject with the disorder, a therapeutically effective amount of reagent which modulates DPC4 expression. For example, in the case of a homozygous deletion of DPC4 alleles, it may be desirable to treat a subject with a DPC4 sense polynucleotide.

In yet another aspect, based on the identification of the chromosomal location of the DPC4 allele, the invention provides a method for detecting the presence or absence of human chromosome 18q21.1 or fragments thereof comprising contacting a sample containing human chromosomal DNA with a polynucleotide of FIG. 3 (SEQ ID NO:1), and detecting the hybridization of the chromosomal DNA with the polynucleotide of FIG. 3 (SEQ ID NO:1).

BRIEF DESCRIPTION OF THE DRAWINGS

FIG. 3 shows the cDNA and deduced amino acid sequence for DPC4 (SEQ ID NO:1 and 2, respectively). The open reading frame starts at nt 129 and ends at nt 1788 (Positions of splice sites immediately follow nt 377 (exons 1/2), nt 552 (exons 2/3), nt 582 (exons 3/4), nt 796 (exons 4/5), nt 915 (exons 5/6), nt 1032 (exons 6/7), nt 1083 (exons 7/8), nt 1267 (exons 8/9),nt 1436 (exons 9/10), nt 1575 (exons 10/11)). The predicted amino acid sequence is shown.

FIG. 4 shows the areas of amino acid sequence similarities among human DPC4, *D. Melangaster Mad* and *C. Elegans* sma-2 (CEM-1). Residues identical to DPC4 are shown in black background; conservative changes are in gray background (Henikoff, et al., *Proc. Natl. Acad. Sci. USA,* 89: 10915, 1992). Gaps introduced for maximal alignment are marked with dashes. Numbers indicate codons positions at which individual alignments begin.

DETAILED DESCRIPTION OF THE INVENTION

Figure 1:
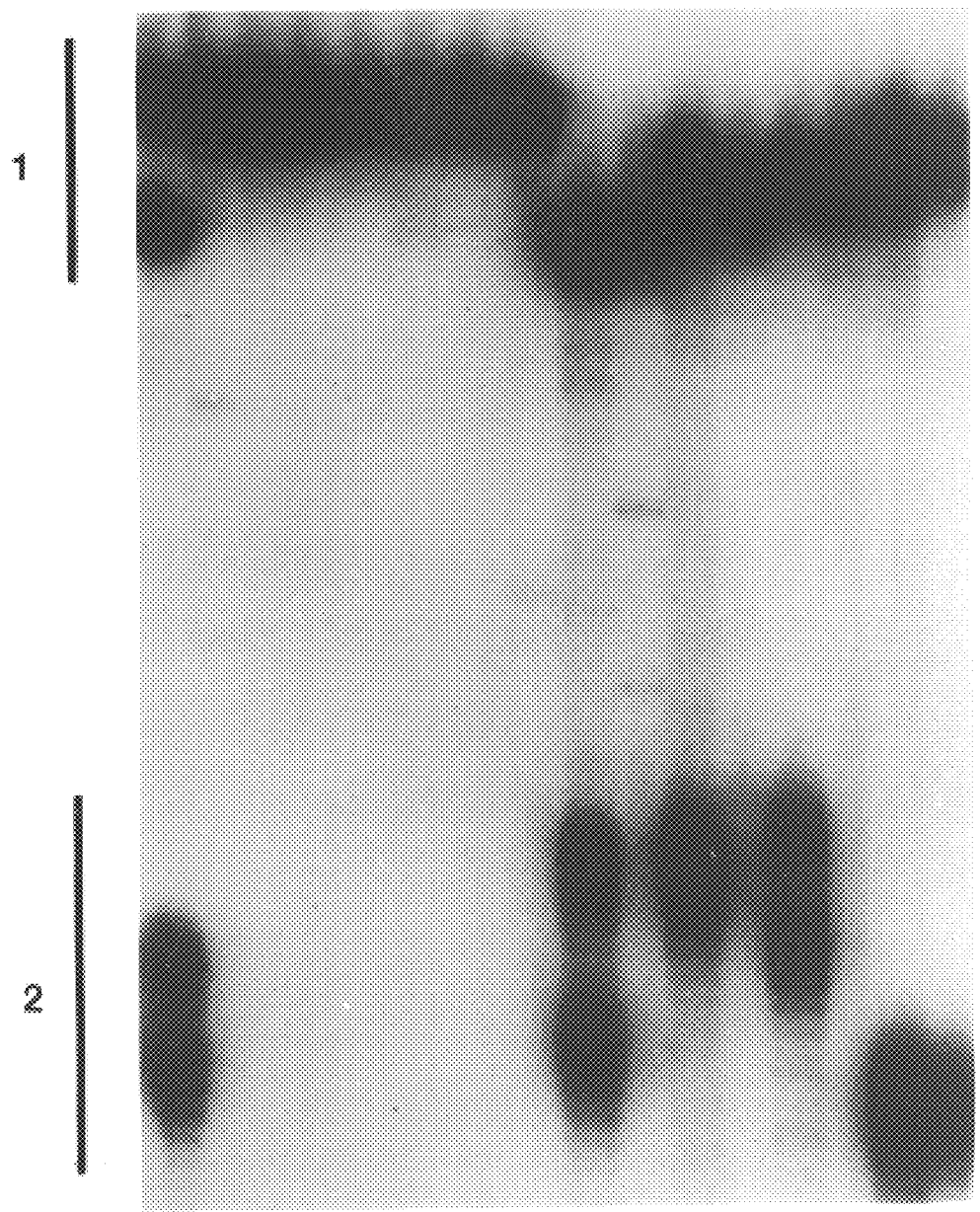
FIG. 1 shows the identification of homozygous deletions identified by multiplex PCR. The smaller product was produced by D18S46, showing homozygous deletion in four cancers. The larger product was from the control locus (D18S68) outside the deletion region. PX16 is represented by seven parallel xenografts. N, Normal DNA, X, Xenograft DNA, C, Control DNA.

The present invention provides a novel tumor suppressor gene, DPC4 (deleted in pancreatic carcinoma, locus 4). DPC4 is located on chromosome 18q21.1, centromeric to DCC, a gene located in the region of 18q LOH.

In a first embodiment, the present invention provides a substantially pure DPC4 polypeptide. DPC4 polypeptide is exemplified by the amino acid sequence shown in FIG. 3 and SEQ ID NO:2. DPC4 polypeptide is characterized as having amino acid sequence similarity to the *D. melanogaster* Mothers against dpp (Mad) gene as well as to the *C. elegans* Mad homologs sma-2, sma-3, sma-4 (CEM-1, CEM-2, CEM-3, respectively). The highest degree of similarity is found among exons 1, 2, and 11 of DPC4 and lesser similarity is found for exons 8, 9, and 10. The decapentaplegic (dpp) gene encodes a growth factor belonging to the transforming growth factor-beta (TGF-β) superfamily and seems to play a central role in multiple cell-cell signaling events throughout development (Hursh, et al., *Development,* 117:1211, 1993). A stop mutation responsible for a phenotype resembling dpp mutants is located at codon 417 within a conserved region of the Mad gene, matches the homologous position of the frameshift mutation found in DPC4 (specimen PX102), and is located one codon 5' to the position of -F. a nonsense mutation found in DPC4 (specimen PX101) (Sekelsky, et al., *Genetics*, 139:1347, 1995).

The term "substantially pure" as used herein refers to DPC4 polypeptide which is substantially free of other proteins, lipids, carbohydrates or other materials with which it is naturally associated. One skilled in the art can purify DPC4 using standard techniques for protein purification. The substantially pure polypeptide will yield a single major band on a non-reducing polyacrylamide gel. The purity of the DPC4 polypeptide can also be determined by amino-terminal amino acid sequence analysis.

The invention includes a functional polypeptide, DPC4, and fumctional fragments thereof. As used herein, the term "functional polypeptide" refers to a polypeptide which possesses a biological function or activity which is identified through a defined functional assay and which is associated with a particular biologic, morphologic, or phenotypic alteration in the cell. Functional fragments of the DPC4 polypeptide, includes fragments of DPC4 as long as the activity, e.g., tumor suppressor activity, of DPC4 remains. Smaller peptides containing the biological activity of DPC4 are included in the invention. The biological function, for example, can vary from a polypeptide fragment as small as an epitope to which an antibody molecule can bind to a large polypeptide which is capable of participating in the characteristic induction or programming of phenotypic changes within a cell. A "functional polynucleotide" denotes a polynucleotide which encodes a functional polypeptide as described herein.

Minor modifications of the DPC4 primary amino acid sequence may result in proteins which have substantially equivalent activity as compared to the DPC4 polypeptide described herein. Such modifications may be deliberate, as by site-directed mutagenesis, or may be spontaneous. All of the polypeptides produced by these modifications are included herein as long as the tumor suppressor activity of DPC4 is present. Further, deletion of one or more amino acids can also result in a modification of the structure of the resultant molecule without significantly altering its activity. This can lead to the development of a smaller active molecule which would have broader utility. For example, it is possible to remove amino or carboxy terminal amino acids which may not be required for DPC4 activity.

The DPC4 polypeptide of the invention also includes conservative variations of the polypeptide sequence. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

The invention also provides an isolated polynucleotide sequence encoding a polypeptide having the amino acid sequence of SEQ ID NO:2. The term "isolated" as used herein includes polynucleotides substantially free of other nucleic acids, proteins, lipids, carbohydrates or other materials with which it is naturally associated. Polynucleotide sequences of the invention include DNA, cDNA and RNA sequences which encode DPC4. It is understood that all polynucleotides encoding all or a portion of DPC4 are also included herein, as long as they encode a polypeptide with DPC4 activity. Such polynucleotides include naturally occurring, synthetic, and intentionally manipulated polynucleotides. For example, portions of the MRNA sequence may be altered due to alternate RNA splicing patterns or the use of alternate promoters for RNA transcription. As another example, DPC4 polynucleotide may be subjected to site-directed mutagenesis. The polynucleotide sequence for DPC4 also includes antisense sequences. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of DPC4 polypeptide encoded by the nucleotide sequence is finctionally unchanged. In addition, the invention also includes a polynucleotide encoding a polypeptide having an amino acid sequence of SEQ ID NO:2 and having at least one epitope for an antibody inmmunoreactive with DPC4 polypeptide.

The polynucleotide encoding DPC4 includes the nucleotide sequence in FIG. 3 (SEQ ID NO:1), as well as nucleic acid sequences complementary to that sequence. A complementary sequence may include an antisense nucleotide. When the sequence is RNA, the deoxyribonucleotides A, G, C, and T of FIG. 3 are replaced by ribonucleotides A, G, C, and U, respectively. Also included in the invention are fragments (portions) of the above-described nucleic acid sequences that are at least 15 bases in length, which is sufficient to permit the fragment to selectively hybridize to DNA that encodes the protein of FIG. 3 (SEQ ID NO:2). "Selective hybridization" as used herein refers to hybridization under moderately stringent physiological conditions.

Specifically disclosed herein is a cDNA sequence for DPC4 which comprises a 1656 bp transcribed sequence (SEQ ID NO:1). The predicted 552 amino acid coding sequence of this gene is characterized by: 1) multiple stop codons in all three reading frames 5' to the putative ATG start site; 2) multiple stop codons in the non-coding frames 3' to the start site; 3) ten splice sites (eleven exons) in the longest possible reading frame; and 4) a terminal TGA stop codon-in-frame, as well as stop codons nearby in the other two frames.

DNA sequences of the invention can be obtained by several methods. For example, the DNA can be isolated using hybridization or computer-based techniques which are well known in the art. These include, but are not limited to: 1) hybridization of genomic or cDNA libraries with probes to detect homologous nucleotide sequences; 2) antibody screening of expression libraries to detect cloned DNA fragments with shared structural features; 3) polymerase chain reaction (PCR) on genomic DNA or cDNA using primers capable of annealing to the DNA sequence of interest; and 4) computer searches of sequence databases for similar sequences.

Preferably the DPC4 polynucleotide of the invention is derived from a mammalian organism, and most preferably from human. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.,* 9:879, 1981).

The development of specific DNA sequences encoding DPC4 can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell to form cDNA.

When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of MnRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., *Nucl. Acid Res.,* 11:2325, 1983).

A cDNA expression library, such as lambda gt11, can be screened indirectly for DPC4 peptides having at least one epitope, using antibodies specific for DPC4. Such antibodies can be either polyclonally or monoclonally derived and used to detect expression product indicative of the presence of DPC4 cDNA.

DNA sequences encoding DPC4 can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the DPC4 polynucleotide sequences may be inserted into a recombinant expression vector. The term "recombinant expression vector" refers to a plasmid, virus or other vehicle known in the art that has been manipulated by insertion or incorporation of the DPC4 genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., *Gene* 56:125, 1987), the pMSXND expression vector for expression in mammalian cells (Lee and Nathans, *J Biol. Chem.,* 263:3521, 1988) andbaculovirus-derivedvectors for expression in insect cells. The DNA segment can be present in the vector operably linked to regulatory elements, for example, a promoter (e.g., T7, metallothionein I, or polyhedrin promoters).

Polynucleotide sequences encoding DPC4 can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

Methods which are well known to those skilled in the art can be used to construct expression vectors containing the DPC4 coding sequence and appropriate transcriptional/translational control signals. These methods include in vitro recombinant DNA techniques, synthetic techniques, and in vivo recombination/genetic techniques. (See, for example, the techniques described in Maniatis et al., 1989 Molecular Cloning A Laboratory Manual, Cold Spring Harbor Laboratory, N.Y.)

A variety of host-expression vector systems may be utilized to express the DPC4 coding sequence. These include but are not limited to microorganisms such as bacteria transformed with recombinant bacteriophage DNA, plasmid DNA or cosmid DNA expression vectors containing the DPC4 coding sequence; yeast transformed with recombinant yeast expression vectors containing the DPC4 coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the DPC4 coding sequence; insect cell systems infected with recombinant virus expression vectors (e.g., baculovirus) containing the DPC4 coding sequence; or animal cell systems infected with recombinant virus expression vectors (e.g., retroviruses, adenovirus, vaccinia virus) containing the DPC4 coding sequence, or transformed animal cell systems engineered for stable expression. Since DPC4 has not been confirmed to contain carbohydrates,both bacterial expression systems as well as those that provide for translational and post-translational modifications may be used; e.g., mammalian, insect, yeast or plant expression systems.

Depending on the host/vector system utilized, any of a number of suitable transcription and translation elements, including constitutive and inducible promoters, transcription enhancer elements, transcription terminators, etc. may be used in the expression vector (see e.g., Bitter et al., 1987, Methods in Enzymology 153:516–544). For example, when cloning in bacterial systems, inducible promoters such as pL of bacterio-phage γ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted DPC4 coding sequence.

In bacterial systems a number of expression vectors may be advantageously selected depending upon the use intended for the expressed protein. For example, when large quantities of DPC4 are to be produced, vectors which direct the expression of high levels of fusion protein products that are readily purified may be desirable. Those which are engineered to contain a cleavage site to aid in recovering are preferred. Such vectors include but are not limited to the *E. coli* expression vector pUR278 (Ruther et al., *EMBO J.* 2:1791, 1983), in which the DPC4 coding sequence may be ligated into the vector in frame with the lac Z coding region so that a hybrid -lac Z protein is produced; pIN vectors (Inouye & Inouye, 1985, Nucleic acids Res. 13:3101–3109; Van Heeke & Schuster, 1989, J. Biol. Chem. 264:5503–5509); and the like.

In yeast, a number of vectors containing constitutive or inducible promoters may be used. For a review see, Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology, Eds. Wu & Grossman, 31987, Acad. Press, N.Y., Vol. 153, pp. 516–544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673–684; and The Molecular Biology of the Yeast Saccharomyces, 1982, Eds. Strathem et al., Cold Spring Harbor Press, Vols. I and II. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. D M Glover, 1986, IRL Press, Wash., D.C.). Alternatively, vectors may be used which promote integration of foreign DNA sequences into the yeast chromosome.

Eukaryotic systems, and preferably mammalian expression systems, allow for proper post-translational modifications of expressed mammalian proteins to occur. Eukaryotic cells which possess the cellular machinery for proper processing of the primary transcript, glycosylation, phosphorylation, and advantageously, secretion of the gene product may be used as host cells for the expression of DPC4. Mammalian cell lines may be preferable. Such host cell lines may include but are not limited to CHO, VERO, BHK, HeLa, COS, MDCK, -293, and WI38.

Mammalian cell systems which utilize recombinant viruses or viral elements to direct expression may be engineered. For example, when using adenovirus expression vectors, the DPC4 coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the protein in infected hosts (e.g.. see Logan & Shenk, 1984, Proc. Natl. Acad. Sci. USA 81: 3655–3659). Alternatively, the vaccinia virus 7.5K promoter may be used. (e,g,, see, Mackett et al., 1982, Proc. Natl. Acad. Sci. USA 79: 7415–7419; Mackett et al., 1984, J. Virol. 49: 857–864; Panicali et al., 1982, Proc. Natl. Acad. Sci. USA 79: 4927–4931). Of particular interest are vectors based on bovine papilloma virus which have the ability to replicate as extrachromosomal elements (Sarver, et al., 1981, Mol. Cell. Biol. 1: 486). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as, for example, the neo gene. Alternatively, the retroviral genome can be modified for use as a vector capable of introducing and directing the expression of the DPC4 gene in host cells (Cone & Mulligan, 1984, Proc. Natl. Acad. Sci. USA 81:6349–6353). High level expression may also be achieved using inducible promoters, including, but not limited to, the metallothionine IIA promoter and heat shock promoters.

For long-term, high-yield production of recombinant proteins, stable expression is preferred. Rather than using expression vectors which contain viral origins of replication, host cells can be transformed with the DPC4 cDNA controlled by appropriate expression control elements (e.g., promoter, enhancer, sequences, transcription terminators, poly-adenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1–2 days in an enriched media, and then are switched to a selective media. A number of selection systems may be used, including but not limited to the herpes simplex virus thymidine kinase (Wigler, et al., 1977, Cell 11: 223), hypoxanthine-guanine phosphoribosyltransferase (Szybalska & Szybalski, 1962, Proc. Natl. Acad. Sci. USA 48: 2026), and adenine phosphoribosyltransferase (Lowy, et al., 1980, Cell 22: 817) genes can be employed in $tk^-$, $hgprt^-$ or $aprt^-$ cells respectively. Also, antimetabolite resistance can be used as the basis of selection for dhfr, which confers resistance to methotrexate (Wigler, et al., 1980, Natl. Acad. Sci. USA 77: 3567; O'Hare, et al., 1981, Proc. Natl. Acad. Sci. USA 78: 1527); gpt, which confers resistance to mycophenolic acid (Mulligan & Berg, 1981, Proc. Natl. Acad. Sci. USA 78: 2072; neo, which confers resistance to the aminoglycoside G-418 (Colberre-Garapin, et al., 1981, J. Mol. Biol. 150: 1); and hygro, which confers resistance to hygromycin (Santerre, et al., 1984, Gene 30: 147) genes. Recently, additional selectable genes have been described, namely trpB, which allows cells to utilize indole in place of tryptophan; hisD, which allows cells to utilize histinol in place of histidine (Hartman & Mulligan, 1988, Proc. Natl. Acad. Sci. USA 85: 8047); and ODC (ornithine decarboxylase) which confers resistance to the ormithine decarboxylase inhibitor, 2-(difluoromethyl)-DL-ornithine, DFMO (McConlogue L., 1987, In: Current Communications in Molecular Biology, Cold Spring Harbor Laboratory ed.).

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the DPC4 of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (see for example, *Eukaryotic Viral Vectors*, Cold Spring Harbor Laboratory, Gluzmnan ed., 1982).

Isolation and purification of microbial expressed polypeptide, or fragments thereof, provided by the invention, may be carried out by conventional means including preparative chromatography and immunological separations involving monoclonal or polyclonal antibodies.

The invention includes antibodies immunoreactive with DPC4 polypeptide or fragments thereof. Antibody which consists essentially of pooled monoclonal antibodies with different epitopic specificities, as well as distinct monoclonal antibody preparations are provided. Monoclonal antibodies are made from antigen containing fragments of the protein by methods well known to those skilled in the art (Kohler, et al., *Nature,* 256:495, 1975).

The term "antibody" as used in this invention includes intact molecules as well as fragments thereof, such as Fab, F(ab')2, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of Athe heavy chain; two Fab' fragments are obtained per antibody molecule;

(3) (Fab')2, the fragment of the antibody that can be obtained by treating whole antibody with the enzyme pepsin without subsequent reduction; F(ab')2 is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, Antibodies: A Laboratory Manual, Cold Spring Harbor Laboratory, N.Y. (1988), incorporated herein by reference).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibodies which bind to the DPC4 polypeptide of the invention can be prepared using an intact polypeptide or fragments containing small peptides of interest as the immunizing antigen. For example, it may be desirable to produce antibodies that specifically bind to the N- or C-terminal domains of DPC4. The polypeptide or a peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, Current Protocols in Immunology, Wiley Interscience, 1994, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

The invention also provides a method for detecting a cell proliferative or developmental disorder associated with DPC4 in a subject, comprising contacting a target cellular component containing DPC4 with a reagent which detects DPC4 and detecting DPC4. The target cell component can be nucleic acid, such as DNA or RNA, or protein. For example, a truncated DPC4 protein, or a homozygous deletion of or intragenic mutation in DPC4 nucleic acid is indicative of such a disorder. When the component is nucleic acid, the reagent is a nucleic acid probe or PCR primer. When the cell component is protein, the reagent is an antibody probe. The probes can be detectably labeled, for example, with a radioisotope, a fluorescent compound, a bioluminescent compound, a chemiluminescent compound, a metal chelator, or an enzyme. Those of ordinary skill in the art will know of other suitable labels for binding to the nucleic acid probe or antibody, or will be able to ascertain such, using routine experimentation.

For purposes of the invention, an antibody or nucleic acid probe specific for DPC4 may be used to detect the presence of DPC4 polypeptide (using antibody) or polynucleotide (using nucleic acid probe) in biological fluids or tissues. Oligonucleotide primers based on any coding sequence region in the DPC4 sequence are useful for amplifying DNA, for example by PCR. Any specimen containing a detectable amount of polynucleotide or antigen can be used. A preferred sample of this invention is tissue of the pancreas, bladder, colon, and blood, urine and intestinal contents and stool. Preferably the subject is human.

Alterations in DPC4 nucleic acid include intragenic mutations (e.g., point mutation, nonsense (stop), missense, splice site and frameshift) and heterozygous or homozygous deletions. Detection of such alterations can be done by standard methods known to those of skill in the art including sequence analysis, Southern blot analysis, PCR based analyses (e.g., multiplex PCR, sequence tagged sites (STSs)) and in situ hybridization. Alterations in DPC4 nucleic acid may be detected as a truncated protein product. Such proteins can be analyzed by standard SDS-PAGE and/or immunoprecipitation analysis and/or Western blot analysis, for example. In addition, the in vitro synthesized (IVS) protein assay as described in the present examples can be used to analyze DPC4 protein product.

Disorders associated with DPC4 that are detectable by the method of the invention include any neoplasm, for example, pancreatic carcinoma, bile duct cancer, bladder cancer, colorectal cancer, Crohn's disease, colitis-associated neoplasia, and chronic ulcerative colitis.

Monoclonal antibodies used in the method of the invention are suited for use, for example, in inrunoassays in which they can be utilized in liquid phase or bound to a solid phase carrier. In addition, the monoclonal antibodies in these immunoassays can be detectably labeled in various ways. Examples of types of immunoassays which can utilize monoclonal antibodies of the invention are competitive and non-competitive immunoassays in either a direct or indirect format. Examples of such immunoassays are the radioimmunoassay (RIA) and the sandwich (immunometric) assay. Detection of the antigens using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The term "immunometric assay" or "sandwich immunoassay", includes simultaneous sandwich, forward sandwich and reverse sandwich immunoassays. These terms are well understood by those skilled in the art. Those of skill will also appreciate that antibodies according to the present invention will be useful in other variations and forms of assays which are presently known or which may be developed in the future. These are intended to be included within the scope of the present invention.

Monoclonal antibodies can be bound to many different carriers and used to detect the presence of DPC4. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such using routine experimentation.

In performing the assays it may be desirable to include certain "blockers" in the incubation medium (usually added with the labeled soluble antibody). The "blockers" are added to assure that non-specific proteins, proteases, or anti-heterophilic immunoglobulins to anti-DPC4 immunoglobulins present in the experimental sample do not cross-link or destroy the antibodies on the solid phase support, or the radiolabeled indicator antibody, to yield false positive or false negative results. The selection of "blockers" therefore may add substantially to the specificity of the assays described in the present invention.

It has been found that a number of nonrelevant (i.e., nonspecific) antibodies of the same class or subclass (isotype) as those used in the assays (e.g., IgG1, IgG2a, IgM, etc.) can be used as "blockers". The concentration of the "blockers" (normally 1–100 $\mu g/(\mu l)$) may be important, in order to maintain the proper sensitivity yet inhibit any unwanted interference by mutually occurring cross reactive proteins in the specimen.

In using a monoclonal antibody for the in vivo detection of antigen, the detectably labeled monoclonal antibody is given in a dose which is diagnostically effective. The term "diagnostically effective" means that the amount of detectably labeled monoclonal antibody is administered in sufficient quantity to enable detection of the site having the DPC4 antigen for which the monoclonal antibodies are specific.

The concentration of detectably labeled monoclonal antibody which is administered should be sufficient such that the binding to those cells having DPC4 is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the individual. The dosage of monoclonal antibody can vary from about 0.001 mg/m$^2$ to about 500 mg/m$^2$, preferably 0.1 mg/m$^2$ to about 200 mg/m$^2$, most preferably about 0.1 mg/m$^2$ to about 10 mg/m$^2$. Such dosages may vary, for example, depending on whether multiple injections are given, tumor burden, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 keV range, which may be readily detected by conventional gamma cameras.

For in vivo diagnosis, radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr, and $^{201}$Tl.

A monoclonal antibody useful in the method of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

The present invention also provides a method for treating a subject with a cell proliferative disorder associated with DPC4. Specifically, the method includes a method of treating a cell proliferative disorder associated with DPC4, comprising administering to a subject with the disorder, a therapeutically effective amount of reagent which modulates DPC4 expression. Alternatively, the method includes administration of a reagent that mimics the action or effect of DPC4. For example, it may be desirable to restore responsiveness of a cancer cell or cell having a DPC4 deletion to a suppressive agent such as TGF-β or member of the TGF-β superfamily pathway by replacing or mimicking the action or effect of DPC4.

TGF-β responsiveness is known to be diminished in many neoplastic cells. In part, this may be due to inactivation of certain cell-cycle regulatory proteins which may mediate these signals (Alexandrow, et al., *Cancer Res.*, 55:1452, 1995; Hannon, et al., *Nature*, 371:257, 1994), or to mutations of TGF-β receptors (Markowitz, et al., *Science*, 268:1336, 1995). In selected chromosomal transfer experiments, only chromosome 18 replacement was able to partially restore TGF-β responsiveness to a cancer cell line (Goyette, et al., *Mol. & Cellul. Biol.*, 12: 1387, 1992), suggesting the presence of an inactivated gene on chromosome 18 which normally would mediate TGF-β suppression.

In pancreatic cancers, for example, the DPC4 nucleotide sequence may be under-expressed as compared to expression in a normal cell due to a mutation or deletion, therefore, it is possible to design appropriate therapeutic or diagnostic techniques directed to this sequence. Thus, where a cell-proliferative disorder is associated with the expression of DPC4 associated with malignancy, nucleic acid sequences that modulate DPC4 expression at the transcriptional or translational level can be used. In cases when a cell proliferative disorder or abnormal cell phenotype is associated with the under expression of DPC4, for example, nucleic acid sequences encoding DPC4 (sense) could be administered to the subject with the disorder.

The term "cell-proliferative disorder" denotes malignant as well as non-malignant cell populations which often appear to differ from the surrounding tissue both morphologically and genotypically. Such disorders may be associated, for example, with absence of expression of DPC4. Essentially, any disorder which is etiologically linked to expression of DPC4 could be considered susceptible to treatment with a reagent of the invention which modulates DPC4 expression.

The term "modulate" envisions increasing or decreasing the expression of DPC4, depending on the indication, when a cell proliferative disorder is associated with under- or overexpression of DPC4 polypeptide, respectively. For example, a sense polynucleotide sequence (the DNA coding strand) encoding DPC4 polypeptide can be introduced into the cell to increase expression of a "normal" DPC4 gene. Antisense nucleic acid can be used to decrease expression of a mutated DPC4 gene.

The present invention also provides gene therapy for the treatment of cell proliferative disorders which are mediated by DPC4. Such therapy would achieve its therapeutic effect by introduction of the appropriate DPC4 polynucleotide which contains a DPC4 gene (sense), into cells of subjects having the proliferative disorder. Delivery of sense DPC4 polynucleotide constructs can be achieved using a recombinant expression vector such as a chimeric virus or a colloidal dispersion system.

Gene therapy methods as described herein can be performed in vivo or ex vivo. In addition, it may be preferable to remove the majority of a tumor prior to gene therapy, for example surgically or by radiation.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). Preferably, when the subject is a human, a vector such as the gibbon ape leukemia virus (GaLV) is utilized. A number of additional retroviral vectors can incorporate multiple genes. All of these vectors can transfer or incorporate a gene for a selectable marker so that transduced cells can be identified and generated. By inserting a DPC4 sequence (including promoter region) of interest into the viral vector, along with another gene which encodes the ligand for a receptor on a specific target cell, for example, the vector is now target specific. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the DPC4 sense or antisense polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include but are not limited to Ψ2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Another targeted delivery system for DPC4 polynucleotide is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 um can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques*, 6:682, 1988).

For use in the diagnostic research and therapeutic applications suggested above, kits are also provided by the invention. Such a kit may comprise a carrier means being compartmentalized to receive in close confinement one or more container means such as vials, tubes, and the like, each of the container means comprising one of the separate elements to be used in the method.

For example, one of the container means may comprise a probe which is or can be detectably labelled. Such probe may be an antibody or nucleotide specific for a target protein or a target nucleic acid, respectively, wherein the target is indicative, or correlates with, the presence of DPC4 of the invention. Where the kit utilizes nucleic acid hybridization to detect the target nucleic acid, the kit may also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radionucleotide label.

Based on the identification of DPC4 at a specific location on chromosome 18, the invention also provides a method for detecting the presence or absence of human chromosome 18q21.1 or fragments thereof comprising contacting a sample containing human chromosomal DNA with a polynucleotide of FIG. 3 (SEQ ID NO:1), or fragments thereof and detecting the hybridization of the chromosomal DNA with the polynucleotide of FIGURE (SEQ ID NO:1). Therefore, DPC4 polynucleotide or STSs as described in the following examples, are useful for analysis of chromosomal mutations or deletions, for example, on chromosome 18, and specifically at 18q21.1.

The invention also provides a method, based on the identification of homozygous deletions of regions of chromosome 18q21.1 flanking DPC4, for treating a subject having a disorder associated with such deletions by administering an agent which would accumulate within or kill a cell having the deletion(s). The agent would be selected based on the absence of production of an enzyme or other product of nearby gene(s) removed by the homozygous deletion. This method focuses on the biochemical difference of certain tumor types compared to the normal cell and represents a target for a chemotherapeutic intervention. This is an example of how the selective absence of a functional copy of a gene contained within a homozygous deletion in cancer might provide a more specific approach to chemotherapy by potentially facilitating the development of drugs toxic to the tumor cell while remaining non-toxic to normal cells.

The following examples are intended to illustrate but not limit the invention. While they are typical of those that might be used, other procedures known to those skilled in the art may alternatively be used.

EXAMPLES

DPC4 represents a highly conserved gene which is frequently inactivated during the development of pancreatic and other types of carcinomas. The following examples show that 28/31 (90%) of pancreatic xenografts had allelic loss to 18q21.1 which included DPC4.25/84 (30%) of pancreatic carcinomas, as well as a bile duct cancer, bladder cancer and colorectal cancer suffered the loss of both DPC4 alleles, thus fulfilling the requirements of Knudson's theory for biallelic inactivation of a tumor-suppressor gene. Intragenic mutations which would be expected to inactivate normal protein function were found in 6/27 (22%) pancreatic carcinomas which lacked homozygous deletions but had allelic loss, again fulfilling the requirements for two inactivating hits. Thus the proportion of cancers with biallelic inactivation was 20/41 (49%) pancreatic xenografts analyzed for both homozygous deletions and mutations.

Example 1

Identification of DPC4

A directed search for deletions which could potentially localize a tumor-suppressor gene on chromosome 18, was initiated using 11 spaced PCR-based markers. A consensus of deletion could not be established from the LOH pattern, since the deletions often spanned most of the chromosomal arm. However, four of 31 xenografts of pancreatic carcinoma had a homozygous deletion involving two contiguous loci (D18S46, D18S363) centromeric to DCC (Data on microsattelite markers, and the corresponding primer sequences, were accessed through the Cooperative Human Linkage Center (http://www.chlc. org/HomePage.html) or from the Human Genome Database (http://gdbwww.gdb.org/)). Multiple sequence-tagged sites (STSs) markers within or flanking the DCC gene showed the deletions to exclude DCC. These results were confirmed in repeated PCRs, in multiplex PCRs, and in several parallel xenografts derived independently from the original primary carcinomas.

Xenograft carcinomas were established as described (Hahn, et al., *Cancer Res.*, 55:4670, 1995). PCR and multiplex PCR conditions for microsattelite markers were as published (Hahn, et al., supra). Southern blot analysis was performed as described (Caldas, et al., *Nat. Genet.*, 8:27, 1994; Seymour, et al., *Cancer Res.*, 54:2761, 1994). STSs used to exclude the involvement of DCC were: SSAV, D18S523, D18S526, D18S101, and the microsattelite marker DCC (Francke, et al., *Cytogenet Cell Genet.*, 66:196, 1994). A homozygous deletion was defined as the absence of a PCR product from a carcinoma DNA template, when compared to a strong product from the paired constitutional DNA template from the same patient. All PCR reactions were repeated at least three times and confirmed by a second primer designed on nearby sequences to exclude the possibility of a primer site polymorphism. The quality of the DNA was further assured by the successful amplification of a 1.8 kb fragment (exons 5–9 of p53) and of numerous primer sets for microsattelite markers.

FIG. 1 shows the identification of homozygous deletions identified by multiplex PCR. The smallerproduct was produced by D18S46, showing homozygous deletion in four cancers. The larger product was from the control locus (D18S68) outside the deletion region. PX16 is represented by seven parallel xenografts. N, Normal DNA, X, Xenograft DNA, C, Control DNA.

Southern blot analysis of three of these cancers revealed an absence of bands in the lanes derived from carcinoma DNA, while bands were presented in constitutional DNA from the same patient, confirming the homozygous deletions. The markers D18S46 and D18S363 were used to screen the CEPH mega-YAC library by PCR (Cone, et al., *Nature*, 366,698, 1993). Seven YAC clones were identified, and in turn two additional overlapping YAC clones were found within the on-line hybridization data of the CEPH database. STSs were derived from isolated YAC ends and served to build a YAC contig (YAC ends were isolated using the inverse PCR technique; Silverman, et al., *PCR Methods and Applications*, 3:141, 1993). Once amplified, the ligation fragments were sequences by cycle sequencing (SequiTerm, Epicentre Technologies) and 20-mer oligonucleotide pairs for sequence-tagged sites (STSs) were designed. The localization to chromosome 18 of all STSs was ensured by PCR analysis of monochromosomal somatic cell hybrid DNA (NIGMS mapping panel 2, Coriell Cell Repositories). Suspected chimeric YACs were excluded from the contig based on this data and the hybridization data from the CEPH database. A tumor panel consisting of 41 xenografts derived from primary pancreatic adenocarcinomas, ten pancreatic cell lines, 22 breast cancer cell lines, and xenografts of four primary biliary cancers and two primary bladder cancers, was screened using STSs derived from the YAC ends and from known markers within the contig. An additional ten homozygous deletions were identified within this tumor panel (six in the pancreatic xenografts, two in pancreatic cell lines, one in the bladder, and in one in the biliary cancer).

Figure 2:
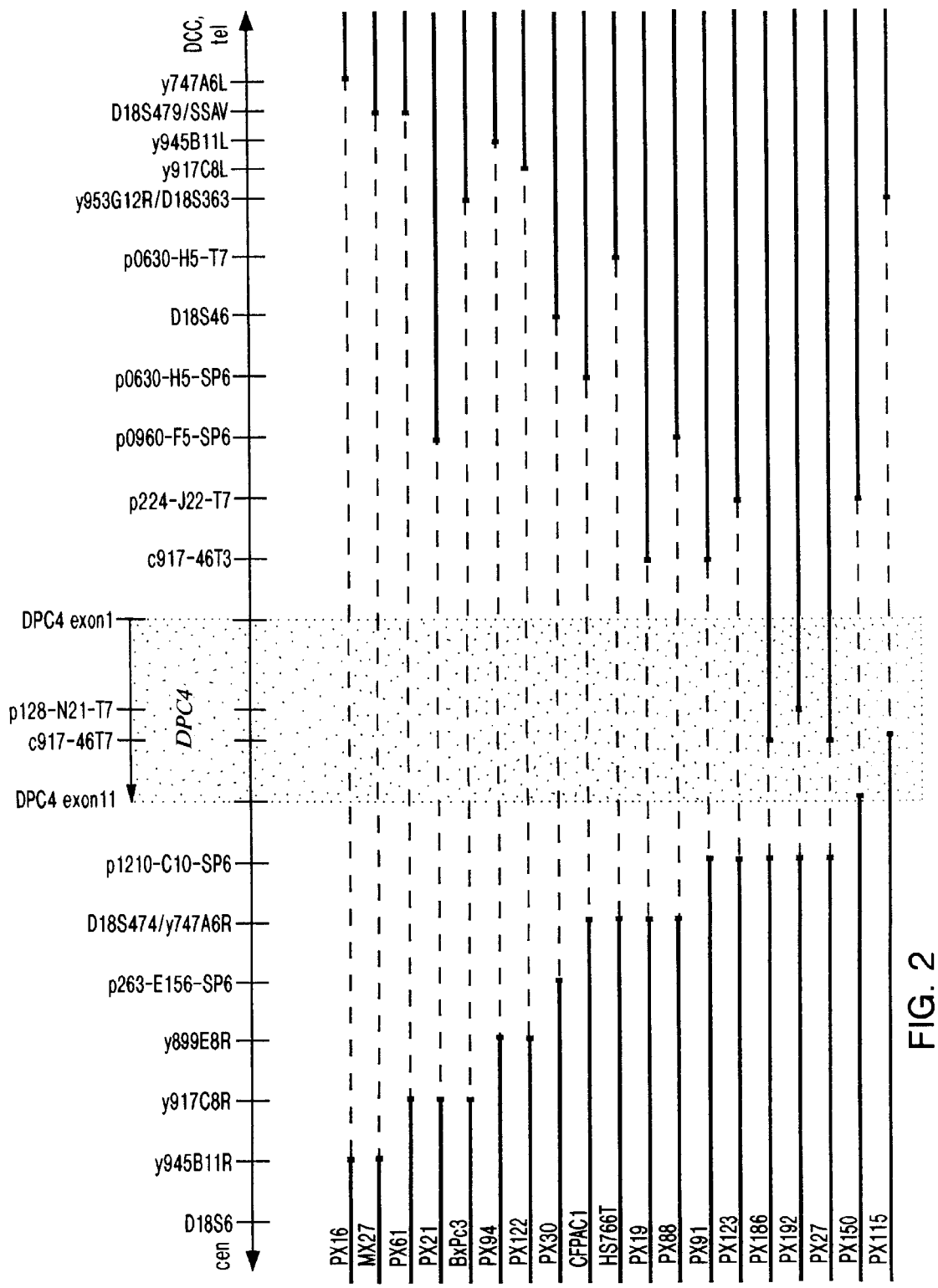
FIG. 2 shows a regional map of the homozygous deletions. Markers are arbitrarily spaced, to reflect relative positions. The shaded area represents the coding region of the DPC4 gene. Suffixes used for markers were "y" for YAC derived markers, "p" for P1/PAC markers and "c" for cosmid markers. The solid lines for each cancer represents the areas without homozygous deletion, all corresponding markers of the map being present. The broken lines represent the areas of homozygous deletion. Cen, direction to centromere; tel, to telomere. All specimen designated with PX represent pancreatic xenografts, except that PX115 is a biliary carcinoma and MX27 is derived from a bladder carcinoma. BxPc3, CFPAC1 and HS766T are pancreatic carcinoma cell lines.

FIG. 2 shows a regional map of the homozygous deletions. Markers are arbitrarily spaced, to reflect relative positions. The shaded area represents the coding region of the DPC4 gene. Suffixes used for markers were "y" for YAC derived markers, "p" for P1/PAC markers and "c" for cosmid markers. The solid lines for each cancer represents the areas without homozygous deletion, all corresponding markers of the map being present. The broken lines represent the areas of homozygous deletion. Cen, direction to centromere; tel, to telomere. All specimen designated with PX represent pancreatic xenografts, except that PX115 is a biliary carcinoma and MX27 is derived from a bladder carcinoma. BxPc3, CFPAC1 and HS766T are pancreatic carcinoma cell lines.

Two of 178 colorectal cancer cell lines and xenografts were also found to harbour a homozygous deletion upon screening with these STSs markers (Leach, et al., supra). The smaller consensus of deletion was now defined by STSs y747A6R and D18S474 on the centromeric end, and D18S46 on the telomeric end. None of the deletions extended beyond YAC-end y747A6L, the telomeric border of the contig. YAC 747A6 also contains the SSAV locus, which is located approximately 2 Mb centromeric to DCC (U. Francke, et aL, *Cytogenet Cell Genet.*, 66:196, 1994). Initiating from the markers D18S46 and D18S474, P1 and PAC library screens were performed, resulting in a contig spanning the consensus region of deletions (A PCR-based P1 screening was performed by Genome Systems, Inc. Using STSs flanking the consensus deletion; positive P1 clones from the Du Pont Merck Pharmaceutical Company Human Foreskin Fibroblast Library #1 (DMPC-HFF#1) were: 1210-C10, 0960-F5 and 0630-H5. A second screen was performed in a human PAC library (purchases from Genome Systems) (Ionannou, et al., *Nat. Genet.*, 6:84, 1994) by hybridizing a random-primer-labeled PCR product to gridded PAC library filters. Positive clones from this screening were: 263-E156, 128-N21 and 224-J22. (Hahn, et aL, supra)). Three YACs, which together spanned the consensus of deletions, were subcloned into a cosmid vector (Partial NdeII-digested YAC DNA was subcloned into the SuperCos-I vector (Stratagene), according to the manufacturer's recommendations. Cosmids were screened and identified by PCR using STSs derived from the region of interest, and sequenced (SequiTerm, Epicentre) using primers specific for vector sequences.) Cosmids were integrated into the P1 /PAC contig, and end sequences from P1s, PACs and selected cosmids were used to define new STS markers (P1/PAC end sequences were generated either by directing sequencing (SequiTherm, Epicentre) or by a PCR-based amplification technique [Liu, et al., *Genomic*, 25:674, 1995). An additional three pancreatic carcinoma xenografts and one pancreatic cell line with homozygous deletions were identified in the above tumor panel, mapping the smallest consensus of deletion to a single cosmid (c917-46).

Using cosmid c917-46, a combination of exon amplification, cDNA library screening, 5'-RACE, and BLAST searches of dbEST, identified three potential expressed sequences (For exon amplification, DNA from cosmid c917-46 was digested with BamHI and BglII and ligated into the pSPL3 exon-trapping vector. The exon-trapping was performed according to the manufacturer's instructions (Gibco/BRL). Exon-trapped sequences were analyzed by BLAST homology searches. The genomic location of the fragments was confirmed by probing against a transfer filter of an EcoRI-digested DNA of cosmid c917-46.5'-RACE was performed according to the manufacturer's instructions (5'-AmpliFINDER RACE kit and human pancreas 5'RACE-Ready cDNA, Clontech). cDNA library screening was performed using exon-trapped sequences or EcoRI restriction fragments from c917-46 as probes. cDNA libraries used were derived from: HeLa cells, human placenta, and human fetal brain (Stratagene), and the human colorectal cancer cell line SW480 (Clontech)). Two of these three sequences were colinear with genomic sequences, showing no splicing, and were not distinguishable from possible unprocessed RNA sequences or DNA contamination of cDNA libraries. The third sequence, from exon amplification, contained a 51 bp open reading frame. Hybridization of this sequence to a human fetal brain cDNA library identified nineteen clones. Sequencing and alignment of these clones revealed a 2680 bp transcript which coded for a previously unknown gene.

FIG. 3 shows the cDNA sequence of DPC4. The open reading frame starts at nt 129 and ends at nt 1788 (Positions of splice sites immediately follow nt 377 (exons 1/2), nt 552 (exons 2/3), nt 582 (exons 3/4), nt 796 (exons 4/5), nt 915 (exons 5/6), nt 1032 (exons 6/7), nt1083 (exons 7/8), nt 1267 (exons 8/9), nt 1436 (exons 9/10), nt 1575 (exons 10/11)). The predicted amino acid sequence is shown. Sequences downstream of nt 2680 were not determined.

Primers designed from the cDNA sequence were then used to sequence the adjoining intronic sequences from the genomic clones (c917-46 and p128-N21). The predicted 552 amino acid coding sequence of this gene was defined by: 1) multiple stop codons in all three reading frames 5' to the putative ATG start site; 2) multiple stop codons in the non-coding frames 3' to the start site; 3) ten splice sites (eleven exons) in the longest possible open reading frame; 4) a terminal TGA stop codons in-frame, as well as stop codon nearby in the other two frames. The gene was termed DPC4 (for: homozygously deleted in pancreatic carcinoma, locus 4).

Four expressed sequence tags (ESTs) derived from the coding region of DPC4 were used to screen 61 pancreatic carcinoma xenografts for additional homozygous deletions specifically involving this candidate gene. Sixty-one pancreatic cancer xenografts were studied further with intragenic markers, comprising the initial panel (excluding the thirteen xenografts found earlier to contain a homozygous deletion) and an additional 33 xenografts. Nine had homozygous deletions, one from the 41 earlier xenografts and eight in the additional 33 xenografts. Thus, 84 pancreatic cancers (74 xenografts and ten cell lines) were studied for homozygous deletions, of which 22 xenografts and three cell line were positive. Nine new homozygous deletions were found. Five had endpoints of deletion within DPC4. Thus, this gene was homozygously deleted in total of 25 (30%) of 84 pancreatic carcinomas.

A screen by an in-vitro synthesized (IVS) protein assay in 14 xenografts detected one case (PX101) with a truncated protein suggestive of an intragenic point mutation (The in-vitro synthesized protein assay was performed essentially as published using the TNT k it (Promega). Primer sequences(5' to 3') were: DPC4S, GGATCCTAATAC-GACTCACTATAGGGCCGCCACCATGGCCTGTC TGAGCATTGTGCATAG (Seq ID NO:3) and DPC4AS, CAGTTTCTGTCTGCTAGGAG (SEQ ID NO:4) M. W. Powell, et aL, *N. Engl. J Med.*, 329:1982, 1993). For all 14 cancers, the RT-PCR product length matched the predicted size, helping to exclude the possibilities of deleted exons of alternative splicing. Genomic sequencing of all eleven exons was performed for 27 pancreatic xenografts not known to harbor a homozygous deletion of DPC4. PCR amplification of the exons was performed as described (Schutte, et al., *Proc. Natl. Acad. Sci. USA*, 92:5950, 1995). Mutations were confirmed in a second PCR reaction. PCR primers (Research Genetics) were: exon 1, DPC4S1, CGTTAGCTGT-TGTTTTTCACTG (SEQ ID NO:5), DPC4AS1, AGAG-TATGTGAAGAGATGGAG (SEQ ID NO:6); exon 2, DPC4S2, TGTATGACATGGCCAAGTTAG (SEQ ID NO:7), DPC4AS2, CAATACTCGGTTTTAGCAGTC (SEQ ID NO: 8); exon 3, DPC4S3, TTTAAAGTAACTATCT-GACTATAC (SEQ ID NO:9), DPC4AS3, GCCCCTAACCTCAAAATCTAC(SEQ ID NO 10); exon 4 DPC4S4, TTTTGCTGGTAAAGTAGTATGC (SEQ ID NO: 11, DPC4AS4, CTATGAAAGATAGTACAGTTAC (SEQ ID NO 12); exons 5 and 6, DPC4S5/6, CATCTTTATAGT-TGTGCATTATC (SEQ ID NO 13), DPC4AS5/6TAATGAAACAAAATCACAGGATG (SEQ ID NO 14); exon 7, DPCS7, TGAAAGTTTTAGCATTAGACAAC (SEQ ID NO 15), DPC4AS7, TGTACTCATCTGAGAAGT-GAC (SEQ ID NO 16); exon 8, DPC4S8TGTTTTGGGTGCATTACATTTC (SEQ ID NO 17), DPC4AS8, CAATTTTTTAAAGTAACTATCTGA (SEQ ID NO 18); exon 9, DPC4S9, TATTAGCATGCTATA-CAATCTG (SEQ ID NO:19), DPC4AS9, CTTCCACCCA-GATTTCAATTC (SEQ ID NO:20); exon 10, DPC4S10, AGGCATTGGTTTTAATGTATG (SEQ ID NO:21), DPC4AS10, CTGCTCAAAGAAACTAATCAAC (SEQ ID NO:22); exon 11, DPC4S11, CCAAAAGTGTGCAGCT-TGTTG (SEQ ID NO:23); DPC4AS11, CAGTTTCTGTCT-GCTAGGAG (SEQ ID NO:24. Sequencing primers were: exon 1, DPC4Ex1, TTTCCAAAGGATCAAAATTGCT-TCAG (SEQ ID NO:25); exon 2, DPC4Ex2, TAATACT-GAGTTGGTAGGATTGTGAG (SEQ ID NO:26); exon 3, DPC4Ex3, CTCACACAAACTAATTCTAGGTCAAC (SEQ ID NO:27); exon 4, DPC4Ex4, GGAGTTTC-CCCCCAAGTGACTAC (SEQ ID NO:28); exon 5, DPC4Ex5, TGAAATCATAAGATGACATCTATGAATG (SEQ ID NO:29); exon 6, DPC4Ex6/1, CTGGACTG-GAAGTAGGACTG (SEQ ID NO:30), DPC4Ex6/2, TCCGGGATGGGGCGGCATAG (SEQ ID NO:31); exon 7, DPC4Ex7, CACTAAATCAATCTAAATACAGGAAATC (SEQ ID NO:32); exon 8, DPC4Ex8, TGTGTTGTGGAGT-GCAAGTGAAAG (SEQ ID NO:33); exon 9, DPC4Ex9, TTTTGACAACAAATAGAGCTTTAAGTC (SEQ ID NO:34); exon 10, DPC4Ex10, GAATTTTCTTTAT-GAACTCATAG (SEQ ID NO:35); exon 11, DPC4Ex11, TATTTTGTAGTCCACCATC (SEQ ID NO:36)).

Six mutations were identified in these 27 cases, including a mutation creating a nonsense codons in exon 11 (PX101), confirming the abnormal translation assay result), a nonsense mutation in exon 8 (PX23) and in exon 9 (PX74), a splice donor site mutation after exon 10 (PX28), an 8 bp frameshift microdeletion (PX102) and a missense mutation producing a nonconservative amino acid substitution (PX86) in exon 11 (Table 1). When exonic sequences were used as primers, mouse DNA templates often gave rise to PCR products of sizes identical to that of human. Therefore, intronic primers were generally used to amplify exons from xenografts). Sequencing of the constitutional DNA from the same patients confirmed that all six mutations were acquired somatically. In both cases in which tumor of the surgical specimen was adequate for sequencing (PX101 and PX102), the mutations found in the xenografts were confirmed in the primary tumor (Microdissection to a neoplastic cell enrichment adequate for direct sequencing could be achieved in two of the six cases having mutations in the DPC4 gene. Non-neoplastic desmoplastic reactions to the carcinomas often limit the cellularity of primary pancreatic carcinomas, precluding direct genetic study (Seymour, et al., supra).

The putative function ofDPC4 is suggested by comparison to known genes of other species. A BLAST (Altschul, et al., *J Mol. Biol.*, 215: 403, 1990; Warren, et al., *Nat. Genet.*, 3: 266, 1993) protein homology search found a high similarity to the *D. Melanogaster* Mothers against dpp (Mad) gene as well as to the *C. Elegans* Mad homologs sma-2, sma-3, sma-4 (CEM-1, CEM-2, CEM-3, respectively). FIG. 4 shows the areas of amino acid sequence similarities among human DPC4, *D. Melangaster* Mad and *C. Elegans* sma-2 (CEM-1). Residues identical to DPC4 are shown in black background; conservative changes are in gray background (Henikoff, et al., *Proc. Natl. Acad. Sci. USA*, 89: 10915, 1992). Gaps introduced for maximal alignment are marked with dashes. Numbers indicate codons positions at which individual alignments begin. The highest degree of similarity was seen among exons 1,2 and 11 of DPC4, and somewhat lesser similarity was found for exons 8,9 and 10 (FIG. 4). In prospholia, homozygous Mad mutant animals exhibit defects in midgut morphogenesis, imaginal disk development, and embryonic dorsal ventral patterning (Sekelsky, et al., *Genetics*, 139:1347, 1995). The decapentaplegic (dpp) gene, which encodes for a growth factor belonging to the transforming growth factor-beta (TGF-β) superfamily, seems to play a central role in multiple cell-cell signaling events throughout development (Hursh, et al., *Development*, 117:1211, 1993). Defects similar to those of the Mad mutants were also seen in the dpp mutant phenotype. It is noteworthy that a stop mutation responsible for this phenotype, located at codons 417 within a conserved region of the Mad gene, matches the homologous position of the frameshift mutation found in DPC4 (PX102), and is located one codons 5' to the position of a nonsense mutation found in DPC4 (PX101) (Table 1) (Sekelsky, et al., supra). A search using the PROSITE database did not identify protein motifs within the predicted protein sequence of DPC4, a finding which is in agreement with an similar analysis of the Mad gene (Sekelsky, et al., supra).

TABLE 1

DPC4 sequence changes in pancreatic carcinomas

| Specimen | Codon(s) | Mutation | Predicted effect |
|---|---|---|---|
| Px23 | 358 | GGA to TGA | Gly to Stop |
| Px74 | 412 | TAC to TAG | Tyr to Stop |
| PX28 | 483 | Agt to Aat | Aberrant splicing |
| Px86 | 493 | GAT to CAT | Asp to His |
| Px101 | 515 | AGA to TGA | Arg to Stop |
| Px102 | 516–518 | CAGAGCTCC to C (SEQ ID NO: 37) | Frameshift |

DPC4 appears to represent a highly conserved gene which is frequently inactivated during the development of pancreatic and other types of carcinomas. This hypothesis was supported by the following observations: First, 28 (90%) of 31 pancreatic xenografts has allelic loss at 18q21.1 which included DPC4. Second, 25 (30%) of 84 pancreatic carcinomas, as well as a bile duct cancer, a bladder cancer and two colorectal cancers, suffered the loss of both DPC4 alleles, thus fulfilling the requirements of Knudson's theory for biallelic inactivation of tumor-suppressor gene. Third, intragenic mutations which would be expected to inactivate normal protein function were found in six (22%) of 27 pancreatic carcinomas which lacked homozygous deletions but had allelic loss, again fulfilling the requirements for two inactivating hits. Thus, the proportion of cancers with biallelic inactivation was 20 (49%) of 41 pancreatic xenografts analyzed for both homozygous deletions and mutations. The functional significance of these point mutations was further supported by the fact that inactivating mutations at the same conserved amino acid positions produced a dramatic phenotype in Drosphilia. Fourth, the remarkable conservation of this gene throughout metazoan evolution may confirm a crucial role in cell growth and/or differentiation. Studies of the DPC4 pathway and its relation to TGF-β effects in pancreatic carcinoma and other model systems should be instructive for the further understanding of the role DPC4 in human neoplasia. The augmentation of TGF-β like pathways through the targeting of control points or effectors which lie downstream of DPC4 in its pathway, may offer a rational strategy for therapeutic manipulation of the abnormal behavior of some human tumors.

Example 2

Deletion Map of DPC4 Region at 18q 21.1

A. MATERIALS AND METHODS

1. Microsatellite analysis. Genomic DNA prepared from 31 xenografted pancreas cancers was typed in a PCR-based assay using 11 commercially available microsatellite markers (Research Genetics, Huntsville, Ala.; specific for chromosomal area 18q. PCRs for microsatellites were performed under the following conditions: 10 μl reaction volume, 1.5 mM $MgCl_2$, 2.0% (v/v) DMSO, 200 μM dATP, dGTP, and dTTP, 5.0 μM dCTP, 0.2 μl α-32P-dCTP (NEN DuPont: 800 Ci/mmole, 10 μCi/μl) in a 1X PCR buffer (Gibco/BRL, Grand Island, N.Y.) with 0.25 μM PCR primers and 0.5 units Taq DNA Polymerase (Gibco/BRL). DNA was amplified for 35 cycles of 95° C. of 15 seconds, 55° C. 30 seconds, and 72°30 seconds in a temperature cycler (Hybaid, Omnigene, Middlesex, UK) using microliter plates, followed by a 5 min. extension at 72° C. The products were separated on a 6.0% polyacrylamide 8M urea gel, and autoradiography performed.

2. Identification of YACs and P1/PACs. Microsatellite markers D18S46 and D18S363 were used in PCR to screen the Genethon megaYAC library (Research Genetics, Huntsville, Ala.). Additional YACs were identified by hybridization data from the on-line "Infoclone" service at Généthon. The DuPont Merck P1 phage library (DMPC-HFF#1) was screened (by Genome Systems, St. Louis, Mo.) using STSs D18S474 and D18S46. A second and third screen was performed in a human PAC library (purchased from Genome Systems, St. Louis, Mo.)(Amemiya, et al., *Nature Genet.*, 6:84, 1994) by hybridization of random-primer-labeled PCR products derived from STSs p0960-F5, p1210-C10 and p128-N21, to gridded PAC library filters.

3. Preparation of a Region-Specific Cosmid Library. Partial NdeII-digested (Boehringer Mannheim, Indianapolis, Ind.) YAC DNA (average fragment of 50 kb) from the region spanning YACs y747B11, y917C8 and y899E8 was subcloned into a BamHI-digested and dephosphorylated SuperCos-1 vector (Stratagene, La Jolla, Calif.), packaged in Phage λ (MaxPlax, Epicentre), and used to infect MR-1 cells (Stratagene). Colonies with human derived inserts were detected by hybridizing filter-lifts to random-primer labeled human Cot-1 DNA (Bio-Rad, Hercules, Calif.). 25 ng of individual cosmid DNAs were spotted on Zeta-Probe GT membranes (Bio-Rad). Region-specific cosmids were isolated by hybridization of end-labeled STS-specific oligonucleotides, and positive clones were confirmed by PCR. Restriction digest analysis indicated an average insert size of 30 kb.

4. Generation of sequence-tagged sites. YAC ends were isolated by an inverse PCR technique (Silverman, G. A., *PCR Methods and Applications,* 3:141, 1993) using a panel of 6 restriction endonucleases (NlaIII, BstUI, Eco0109, HaeIII, TaqI and BanII: New England Biolabs, Beverly, Mass.). Once amplified, the ligation fragments were sequenced by cycle sequencing (SequiTerm, Epicentre Technologies, Madison, Wis.) and 20-mer oligonucleotide pairs for sequence-tagged sites (STSs) were designed. P1/PAC end sequences were generated either by direct sequencing (SequiTherm, Epicentre) or by a PCR-based amplification technique using slow ramping of the annealing temperature (Liu, et al., *Genomics,* 674: 1995). Selected cosmid insert ends were sequenced (SequiTerm, Epicentre) using primers specific for vector sequences. The localization to chromosome 18 of all STSs was ensured by PCR analysis of monchromosomal somatic cell hybrid DNA (NIGMS mapping panel 2, Coriell Cell Repositories). Suspected chimeric YACs were excluded from the contig based on this data and the hybridization data from the CEPH database. The primer sequences are shown in Table 2.

5. Homozygous Deletion Mapping by STSs. Sequence-tagged sites (STSs) were amplified using 40 ng of genomic DNA in 67 mM Tris-HCl pH 8.8, 4 mM $MgCl_2$, 16 mM $(NH_4)_2SO_4$, 10 mM 2-mercaptoethanol, 100 g/ml bovine serum albumin, 200M each dATP, dCTP, dGTP and dTTP, 1 μM each primer and 2 units of Taq polymerase (Gibco-BRL), in a final reaction volume of 15 μl. The enzyme was added after a pre-heating step of 2 minutes at 94° C. Thirty cycles of 94° C. for 30 seconds, 58° C. for one minute and 72° C. for one minute, were followed by a final extension of 5 minutes at 72° C. A homozygous deletion was defined as the absence of a PCR product from a carcinoma DNA template, when compared to a strong product from the paired constitutional DNA template from the same patient. All PCR reactions were repeated at least three times and confirmed by a second primer pair designed on nearby sequences to exclude the possibility of a primer site polymorphism. The quality of the DNA was further assured by the successful amplification of a 1.8 kb fragment (exons 5–9 of p53)and of numerous primer sets for microsatellite markers.

B. Results

Figure 5:
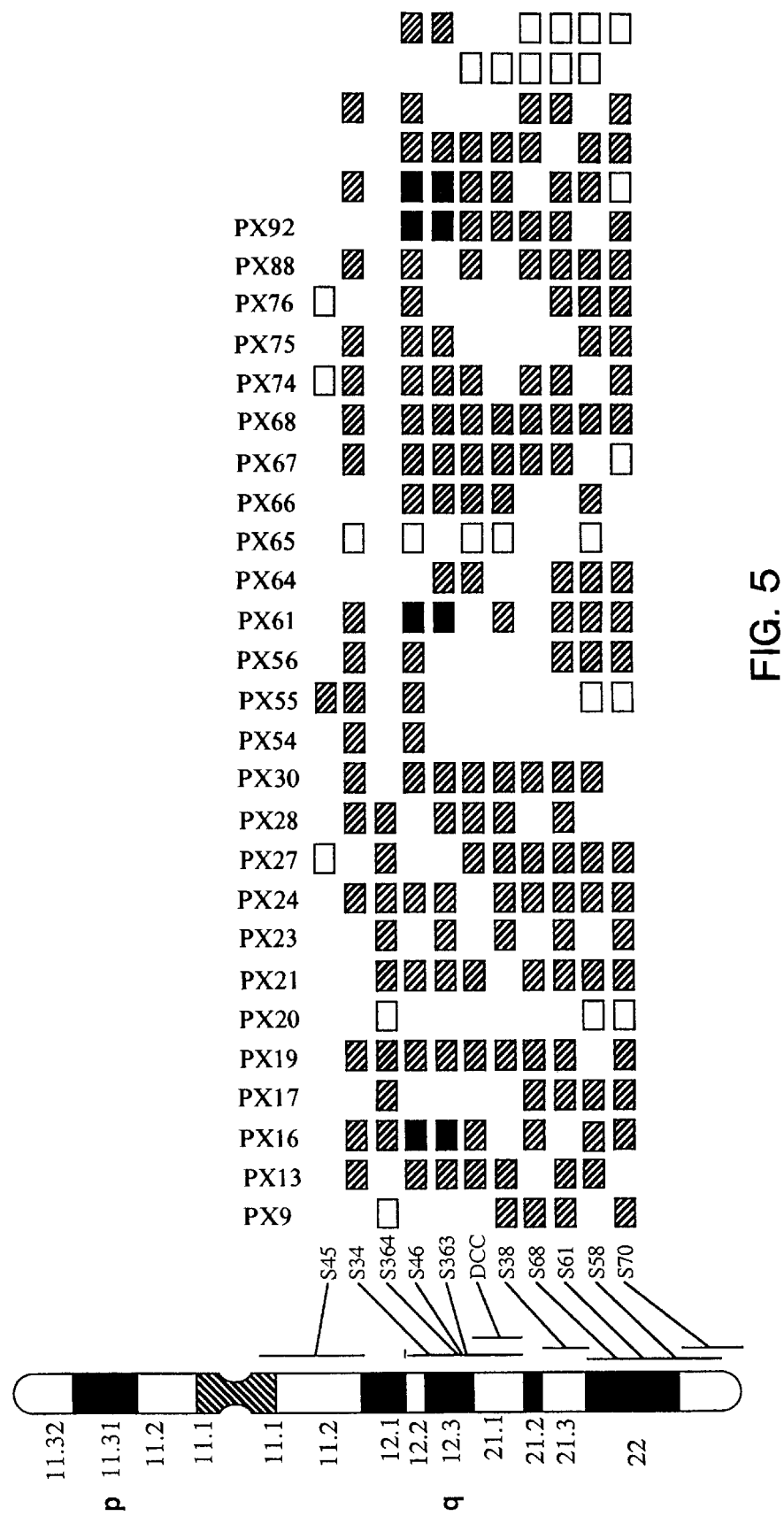
FIG. 5 shows the chromosome 18 deletion map. Black rectangle, homozygous deletion; Striped rectangle, loss of heterozygosity; White rectangle, retention of heterozygosity; empty spaces represent uninformative marker loci. PX refers to a pancreatic xenograft and is followed by an identification number.

Allelic Loss Analysis and the Identification of Homozygous Deletions. Allelic loss at 18q was identified in 28 (91%) of 31 pancreatic cancers. FIG. 5 shows a chromosome 18 deletion map. Black rectangle, homozygous deletion; Striped rectangle, loss of heterozygosity; White rectangle, retention of heterozygosity; empty spaces represent uninformative marker loci. PX refers to a pancreatic xenograft and is followed by an identification number. The smallest consensus of allelic loss among the 31 cases mapped between markers D18S364 and D18S68. Two markers, D18S46 and D18S363, were homozygously deleted in four pancreatic cancer xenografts (PX16, PX61, PX92 and PX94). The homozygous deletions were confirmed by multiplex PCR and by Southern blot analysis. Marker D18S46 had been localized centromeric to DCC by radiation hybrid mapping (Francke, etal., *Cytogenet. Cell Genet.*, 66:196, 1994), whereas marker D18S363 was not unambiguously placed in relation to D18S46 nor to DCC at that time. The microsatellite marker DCC within the DCC gene (at nt 1432, Risinger, et al., *Human Mol. Genet.,* 1:657, 1992) was not homozygously deleted in any of the cases. To conclusively exclude the DCC region, the four cases having homozygous deletion were further analyzed with markers SSAV, D18S523, D18S526, D18S101, all known to map centromeric to DCC (Francke, et al., supra) and telomeric to D8S46. All four cases were shown not to involve the DCC region, confirming the localization of the new locus centromeric to DCC. The locus was termed DPC4 for "Deleted in Pancreatic Carcinoma, locus 4".

Isolation and Analysis of YAC Clones from the DPC4 Region. To generate a physical map from the DPC4 region, the CEPH mega YAC library was screened with markers D18S46 and D18S363. Seven YAC clones were identified (y957B11, y747E1, y953G12, y945B11, y917C8, y899E8 and y747A6). All YACs except y953G12 and y747E1 were positive for both markers, establishing the proximity of the markers D18S46 and D18S363. Two additional linking YACs (y779A10 and y790A2) were identified from the Généthon on-line database (Infoclone). The initial physical map comprised the nine YAC-end STSs, microsatellite markers mapping to these YACs as given in the CEPH database (D18S474 and D18S479), and the above-mentioned markers localized centromeric to DCC. The composite YAC contig map is shown in FIG. 6. YAC y747E1 appeared to be chimeric, since neither of its end sequences mapped to chromosome 18. The centromeric end of YAC y953G12 similarly could not be placed on chromosome 18. The YACs y779A10, y790A2 and YAC y747A6 were positive for marker SSAV but were negative for additional markers mapping between the SSAV locus and the DCC locus (D18S523, D18S526, D18S101), thus establishing the telomeric border ofthe contig. The depth of the contig at the region of interest was five YACs (excluding chimeric YAC y747E1).

Figure 6A:
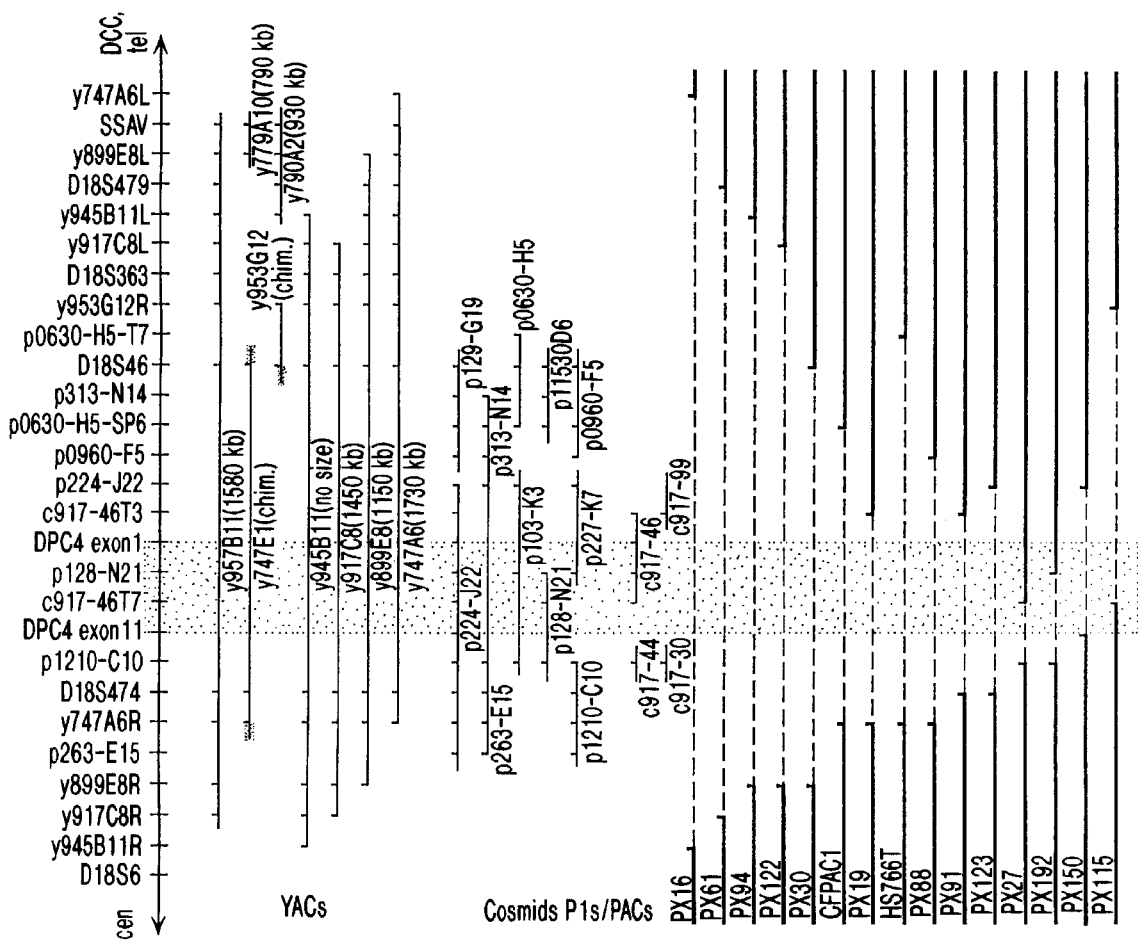
FIGS. 6a, b, and c show a physical map and homozygous deletion boundaries of the DPC4 region at chromosome 18q21.1. Shaded area, DPC4 gene region. Physical Map: The STSs, including D18S markers are positioned based on the data from the YAC, P1/PAC and cosmid clones and the mapping data from the homozygous deletions in pancreatic carcinomas. Sizes of clones are not in scale and the relative distance of the STS markers is arbitrary, reflecting relative position. Small vertical ticks, on the clones, presence of the corresponding STS. STS content of YAC and P1/PAC clones was tested only for selected markers, chim, chimeric YAC, Grey shaded YAC ends, represents chimeric YAC clones ends. Deletion Map: The solid line for each cancer represents the areas without homozygous deletion, all corresponding markers of the map being present. The broken line represents the area of homozygous deletion. cen, direction to centromere; tel, direction to telomere. Tumor samples designated with PX represent pancreatic cancer xenografts, except, PX115 in a carcinoma of the distal common bile duct arising in the pancreas, CFPAC1 and HS766T are pancreatic carcinoma cell lines. Only cases which were important to the mapping of STSs or for the definition of the consensus of homozygous deletions are shown. For STS primer sequences refer to Table 2.
Figure 6B:
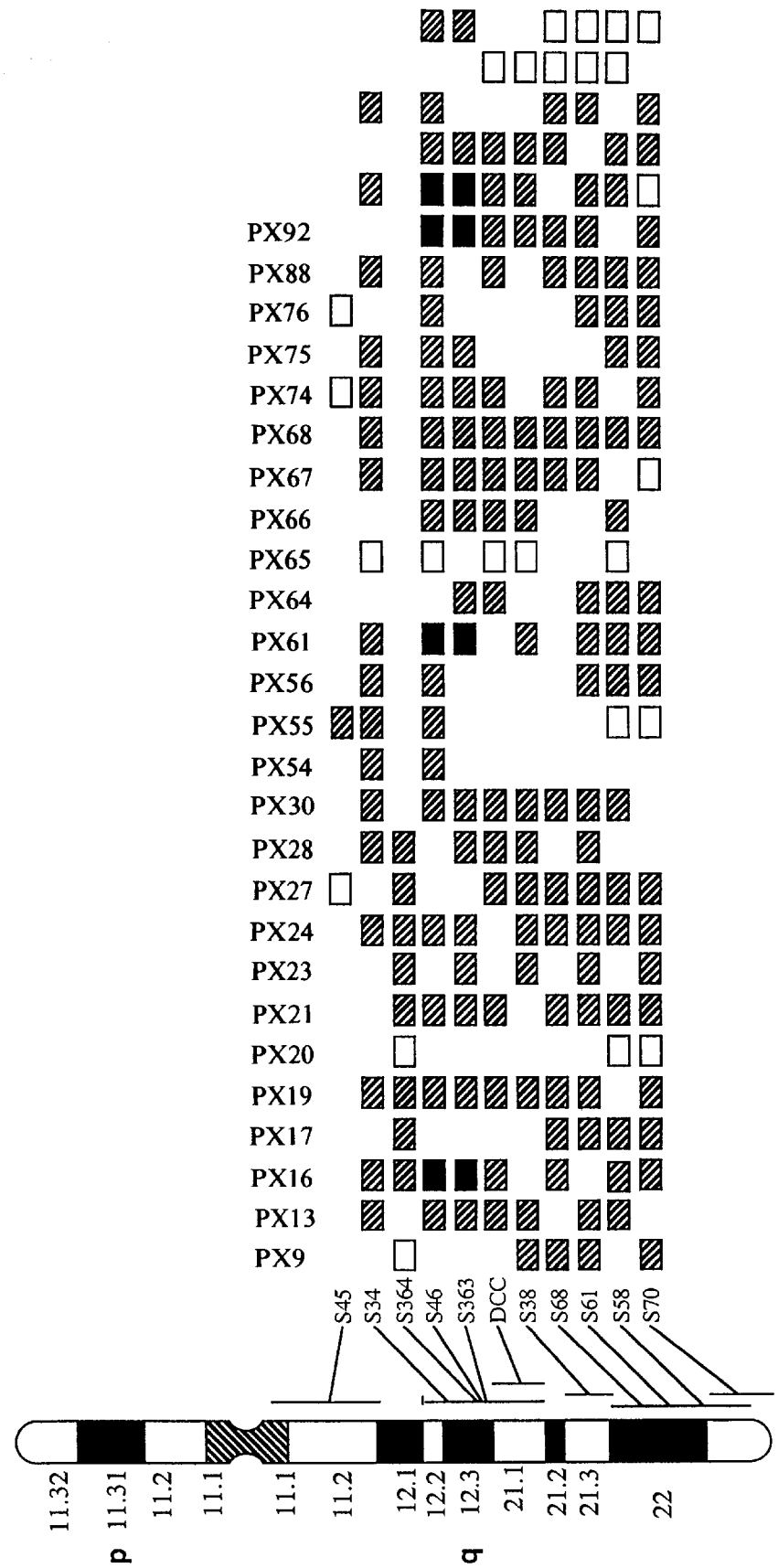
Figure 6C:
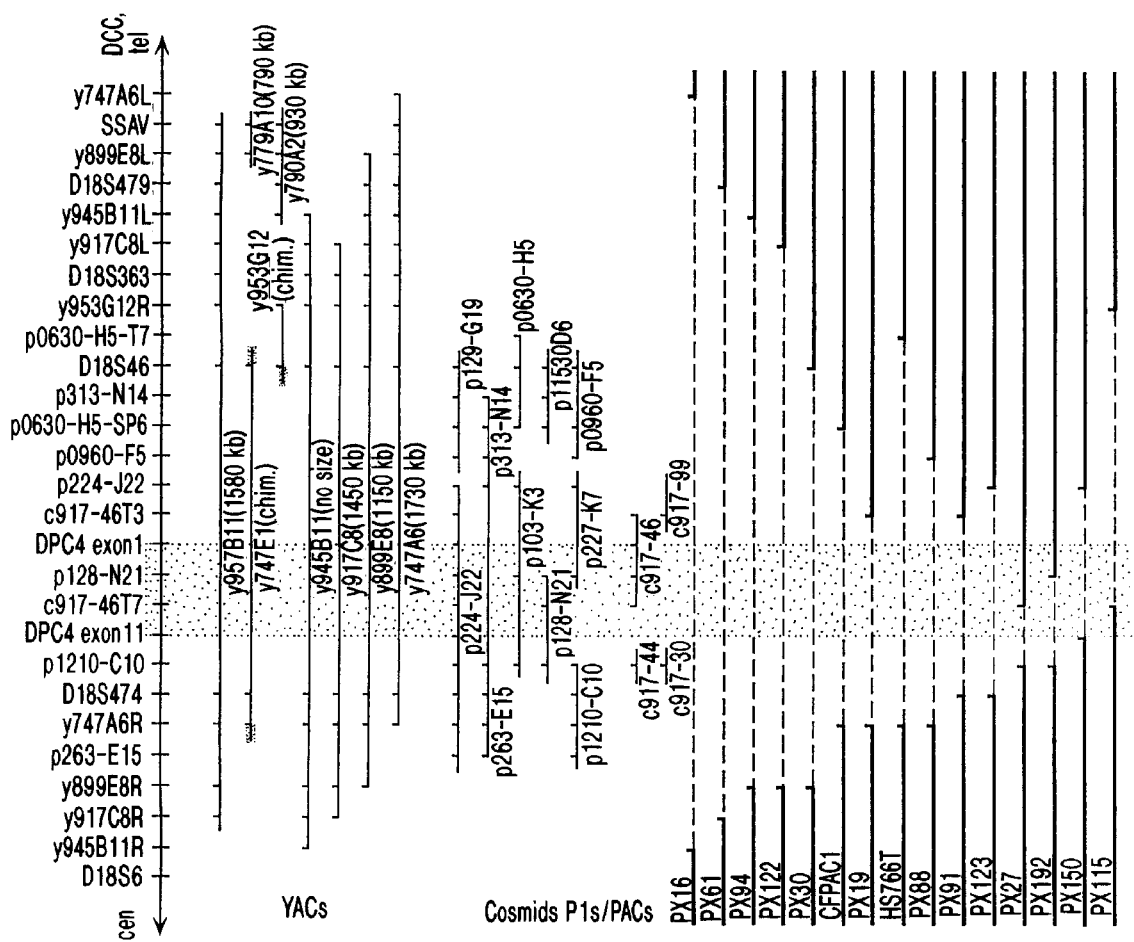

Isolation and Analysis ofP1/PAC Clones from the DPC4 Region. All STSs from the YAC contig were applied to map the extent of the four identified homozygous deletions relative to the contig. Further, the markers within and closest to the consensus region of homozygous deletions were used to screen an "extended" panel of tumors (41 xenografts derived form primary pancreatic adenocarcinomas, ten pancreatic cell lines, 22 breast cancer cell lines, and xenografts of four primary biliary cancers and two primary bladder cancers). An additional 10 homozygous deletions were identified. The centromeric end of the consensus of homozygous deletions was now defined by marker D18S474 and the telomeric end by D18S46. FIGS. 6a, 6b, and 6c show a physical map and homozygous deletion boundaries of the DPC4 region at chromosome 18q2 1.1. Shaded area, DPC4 gene region. Physical Map: The STSs, including D18S markers are positioned based on the data from the YAC, P1/PAC and cosmid clones and the mapping data from the homozygous deletions in pancreatic carcinomas. Sizes of clones are not in scale and the relative distance of the STS markers is arbitrary, reflecting relative position. Small vertical ticks, on the clones, presence of the corresponding STS. STS content of YAC and P1/PAC clones was tested only for selected markers, chim, chimeric YAC, Grey shaded YAC ends, represents chimeric YAC clones ends. Deletion Map: The solid line for each cancer represents the areas without homozygous deletion, all corresponding markers of the map being present. The broken line represents the area of homozygous deletion. cen, direction to centromere; tel, direction to telomere. Tumor samples designated with PX represent pancreatic cancer xenografts, except, PX115 in a carcinoma of the distal common bile duct arising in the pancreas, CFPAC1 and HS766T are pancreatic carcinoma cell lines. Only cases which were important to the mapping of STSs or for the definition of the consensus of homozygous deletions are shown. For STS primer sequences refer to Table 2. The two STSs, D18S474 andD18S46, were usedto initiate a P1 walk from both sites of the contig. Six P1 clones were identified. Selected P1s were used to generate eight end-sequence specific STSs. The mapping of these STSs to the contig and another round of tumor screening identified STS p1210-C10 and pO960-F5 as the borders of a new consensus of homozygous deletions. A second walk performed with these STSs found two linking PACs (p224-J22 and p313-N14) establishing a complete contig between markers D18S474 and D18S46. A third PAC library screen was performed to increase the coverage at the area of the link between the two PACs (p224-J22 and p313-N14) and to exclude larger interstitial deletions (cloning artifacts) as the reason for the link, thus two additional PACs (p103-K3 and p227-K7) were identified confirming the contig. End sequence-specific STSs were again used to screen the tumor panel. One STS (p128-N21) was found to be deleted in all cases, and the markers flanking the new consensus of deletion were thus p224-J22 and p1210-C10, also narrowing the consensus to the size of one PAC (p224-J22).

Isolation of Cosmids from the DPC4 Region and Gene Identification. These three STSs (p128-N21, p224-J22, and p1210-C10) were used to screen filters of the cosmid minilibrary of the region. Four cosmids were found, mapped, and used to generate new STSs (FIG. 6). STSs specific for the telomeric ends of cosmid c917-46 were retained in PX19 and PX9. PX115 showed the retention of the centromeric end STS of c917-46. The STS p128-N21, located within cosmid c917-46, was deleted in all cases including the three mentioned above, therefore localizing the consensus of homozygous deletion to this cosmid. Using c917-46, a combination of exon amplification, cDNA library screening, 5'-RACE, and BLAST database searches of dbEST, we identified a novel candidate tumorsuppressor gene, DPC4 was identified. STS c917-46-T7 is located in exon 8 of DPC4 and STS p128-N21 is located 5' to exon 7 and within an intron of the DPC4 gene. The study of the ESTs derived from DPC4 exons 1 and 11, and STS c917-46-T7 and p128-N21, identified 25 (30%) of 84 pancreatic carcinomas (41 pancreatic xenografts and 10 pancreatic cancer cell lines of the "extended" panel and additional, recently established 33 pancreatic xenografts) to have homozygous deletions involving the DPC4 gene. Together, 24 STSs could be unambiguously ordered within the DPC4 region. A complete list of the STS primer sequences is given in Table 2.

Summarized homozyous deletion status in pancreatic carcinomas. There are two previously published loci known to be homozygously deleted in pancreatic carcinoma, DPC1/2 at 13.q12 (Schutte, et al., *Proc. Nati. Acad. Sci. USA*, 92:595, 1995) and p16 (DPC3) at 9p21 (Kamb, et aL, Science (Washington D.C.), 264:43 6, 1994). In a series of 36 pancreatic carcinomas studied for both loci and including DPC4 at 18q21.1, the p16 locus and the DPC4 locus revealed the highest frequency of homozygous deletions (42% and 39%, respectively) (Caldas, et al., *Nature Genet.*, 8:27, 1994). Homozygous deletions at any of the three loci identified in 23 (64%) of 36 pancreatic cancers (Table 3).

The locus at 18q21.1 was identified as being frequently homozygously deleted in pancreatic carcinoma. From this locus, termed DPC4, an integrated high resolution physical map was constructed and led to the discovery of a new candidate tumor-suppressor gene, DPC4 (Hahn, et al., supra). The map of this region described here, contains twenty-four STSs derived from YAC, P1/PAC and cosmid end sequences, including four microsatellites. The STSs were localized in an unambiguous order over an approximately 2 Mb region chromosome 18q21.1.

Although the initial purpose of the physical map is fulfilled, the generated STSs and their localization are important for the definition of the boundaries and gene content of the homozygous deletions in pancreatic carcinoma and other tumor types, a knowledge which could be useful for cancer therapy. Inactivated tumor-suppressor genes and homozygous deletions both result in clones of cells lacking functional copies of specific genes. In other words, homozygous deletions both result in clones of cells lacking functional copies of specific genes. In other words, homozygous deletions and inactivated tumor-suppressor genes can help to establish an absolute biochemical differences (except in the cases of redundant protein function) between neoplastic and non-neoplastic cells. The knowledge of these differences in various cancer types could be instrumental in devising therapeutic strategies.

well-characterized set of cases, and extensive molecular genetic profiles have been published (Kern, et al., *Gastroenterol*, 107:420, 1994; Redston, et al., *Gastroenterology*, 108:383, 1995). Clinical information about the patients was obtained from chart review. Lesions were classified according to the 1983 Inflammatory Bowel Disease-Dysplasia Morphology Study Group Criteria (IBD-DMSGC), and diagnosis were confirmed by at least four experienced gastrointestinal pathologists (Kern, et al., supra; Redston, et al., supra). Specimens were stored at −80° C. prior to analysis. All specimens were cryostat-directed to confirm the diagnosis of the tissues being examined, and to enrich for lesional cellularity (Sckelsky, et al., *Genetics*,

TABLE 2

STSs

| Primer ID/ Size Locus[a] (bp) | Primer sequence sense (5'–3') (SEQ ID NO: 38–64) | | | | | | | Primer sequence Antisense (5'–3') (SEQ ID NO: 65–91) | | | | | | | |
|---|---|---|---|---|---|---|---|---|---|---|---|---|---|---|---|
| y945B11R | CAG | AAT | AGA | AGG | ATG | GTG | AC | AGT | TAC | CCT | GTT | GTG | CTA | TC | 111 |
| y945B11L | AAT | TGA | CAG | GCA | GCA | AGT | AG | ATG | TGT | ACC | CAG | AAG | GAA | AG | 123 |
| y917C8R | GCA | CAT | TTG | GAT | TCT | ATC | TAG | CTC | CTT | GCC | TTA | AAG | AAT | CAG | 150 |
| y917C8L | AGG | GCC | TGG | CAG | TAT | GAA | AG | ATG | CAG | GCC | CIT | CAC | AGA | C | 141 |
| y899E8R | ATT | GGT | TTC | TCC | AGA | GTT | TTG | TTG | TTC | CTC | TCT | CAT | GAT | TTG | 136 |
| y899E8I | ATT | ATG | GTG | GTT | TAA | AGA | CAT G | GTG | CAT | AAT | GCC | GAA | TGT | TC | 139 |
| y747A6R | CAT | CTC | ATT | TGA | ATT | TGA | GAA AG | TAA | GAT | CIT | TTC | ATT | GGA | TTA TG | 103 |
| y747A6L | AAA | TCA | GTT | GTA | TTT | CTA | TTC AC | TCT | TGA | CTT | TIT | CAG | AAG | TGT TG | 137 |
| y953G12R | GTG | GTC | TGG | AGA | GTC | TAA | AC | TAC | CTT | GGC | TGC | CAA | ACA | TC | 180 |
| p263-E15 | ATG | GGC | TTA | TAA | CTG | TGA | TAG | CIT | ACA | ACA | ATG | CTA | GTA | AGA | 96 |
| p1210-C10 | TCC | CCT | TCA | CAG | CTA | GCA | AG | TCA | TIT | TCG | CAC | AGG | CAA | AC | 88 |
| p128-N2I | GCT | TTG | TAA | CTT | GCT | TTG | ATT C | CTG | GCT | AAA | CTT | CCC | AAA | TG | 161 |
| p224-J22 | CTG | CAG | CTC | TGT | GAG | ATG | | TCA | CTC | CTT | ACT | AGC | TAT | G | 102 |
| p313-N14 | TTA | TAC | CAA | TTA | TGG | GAA | ACA G | AAT | TAA | AAT | TCA | CAA | CAA | TAG TG | 84 |
| p0630-H5-SP6 | GCC | TGC | AAC | ACA | CAA | TIT | AC | GAG | GGC | AGG | AAA | GGA | AAT | AC | 122 |
| p0630-H5-T7 | CCG | TAC | CTG | GCC | AGA | AGT | C | ATG | ACA | TGA | TGG | TGA | TGA | TTT G | 93 |
| p0960-F5 | TCC | CAA | AGT | GCT | GGG | ATT | TC | GTG | AGT | TGC | TGG | GAT | TAG | AG | 121 |
| c917-46-T3 | GTT | CTG | CAG | TGA | AAT | TGG | TG | ACA | GCA | GTT | TGG | GAC | AAG | TG | 63 |
| c917-46-T7 | GTC | CAC | GTA | TCC | ATC | AAC | AG | CTT | ACT | TTG | AAA | TGG | ATG | TTC AG | 86 |
| D18S6 | TGA | ACT | AAT | AGC | CAA | GAA | CT | AAT | CTA | CCT | TGC | TAG | GAA | T | 900 |
| D18S474 | TGG | GGT | GTT | TAC | CAG | CAT | C | TGG | CTT | TCA | ATG | TCA | GAA | GG | 119–139 |
| D18S46 | GAA | TAG | CAG | GAC | CTA | TCA | AAG AGC | CAGATT | AAG | TGA | AAA | CAG | CAT | ATG TG | 129–153 |
| D18S363 | GCT | TCA | TTC | TCT | CAC | TGG | AT | TTG | GGA | ACT | GCT | CTA | CAT | TC | 117–247 |
| D18S479 | AAT | GCC | CAG | CAG | AGT | G | | AGT | GGT | TTG | ACA | GAG | AGT | GC | 294–304 |
| DPC4exon1 | TGT | CTG | AGC | ATT | GTG | CAT | AG | AAG | CCT | CCC | ATC | CAA | TGT | TC | 201 |
| DPC4exon11 | AGA | AAC | ACC | TTG | CTG | GAT | TG | CAG | TIT | CTG | TCT | GCT | AGG | AG | 262 |
| SSAV | ATA | CAT | GGC | TTT | CCT | GGG | CAG | CCT | CCG | CTG | TGA | CGG | TGT | CCA | 430 |

[a]D18S markers and SSAV marker are described in Francke, et al., supra; Weber, et al, Am. J. Hum. Genet., 44:388, 1989; and Gyapay, et al., Nature Genet., 7:246, 1994 respectively. Suffixes used for markers were "y" for YAC derived markers, "p" for P1/PAC markers and "c" for cosmid markers. Physical localization of all markers is shown in FIG. 2.

TABLE 3

Homozygous deletions in pancreatic carcinomas[a].

| | |
|---|---|
| One known homozygous deletion: | 16 |
| Two known homozygous deletions: | 7 |
| One or more homozygous deletions: | 23 of 36 (64%) |

[a]Summarized are 36 pancreatic carcinomas studies for homozygous deletions at three loci, DPC1/2, p16 gene, and DPC4.

Example 3

Mutational Involvement of DPC4 In Colitis-Associated Neoplasia

1. Patients and Specimens

Specimens were obtained from six cases of colitis-associated neoplasia that were resected at The Johns Hopkins Hospital between the years 1989–1993. This is a well-characterized set of cases, and extensive molecular 139:1347, 1995). All cryostat-dissected samples examined could be enriched to this cellularity. DNA was prepared as previously described (Bos, et al., *Nature*, 327:293, 1987). For each patient, the most advanced lesion sampled for the frozen tissue bank was examined for mutations. For CC-6, two histologically distinct areas of a carcinoma were analyzed.

2. DPC4 Mutation Detection

PCR amplification of each exon, exons 1 through 11, was done with primers as described in Example 2. Cycle sequencing of the PCR products was done by the SequiTherm kit (Epiccentre Technologies). Abnormal sequences were confirmed by sequencing of the product of a second independently amplified PCR product and by sequencing the PCR product in the opposite direction using another primer. Non-neoplastic mucosa was sequenced at the site of mutations, to establish the somatic nature of the mutations.

The clinical and pathologic characteristics of the patients, previously published, are reviewed in Table 4. One patient (CC-1) had pathological findings that could not be easily differentiated from those seen in sporadic colorectal neoplasia. One patient (CC-2) also had sclerosing cholangitis.

TABLE 4

Clinical Characteristics of Patients and Summary of Mutations

| Sample | Age at operation (yrs) | Type | Duration of colitis Extent | (yrs) | Site/Lesion | |
|---|---|---|---|---|---|---|
| CC-1 | 71 | UC | Unknown | 16 | Rectum | Dukes' C nonmucinous carcinoma |
| CC-2a | 45 | UC | Pancolitis | >10 | Ascending | Dukes' C nonmucinous carcinoma |
| CC-3 | 40 | CD | Pancolitis | 25 | Rectum | Dukes' B mucinous carcinoma |
| CC-4 | 45 | UC | Pancolitis | >20 | Anorectum | Plaque of high-grade dysplasia. No carcinoma |
| CC-5a | 58 | CD | Pancolitis | 37 | Rectum | Dukes' A mucinous carcinoma |
| CC-6a | 35 | UC | Pancolitis | 12 | Ascending | Dukes' C carcinoma, nonmucinous area |
| CC-6b | | | | | | Dukes' C carcinoma, incucinous area |

UC, Ulcerative Colitis; CD, Crohn disease

Figure 7:
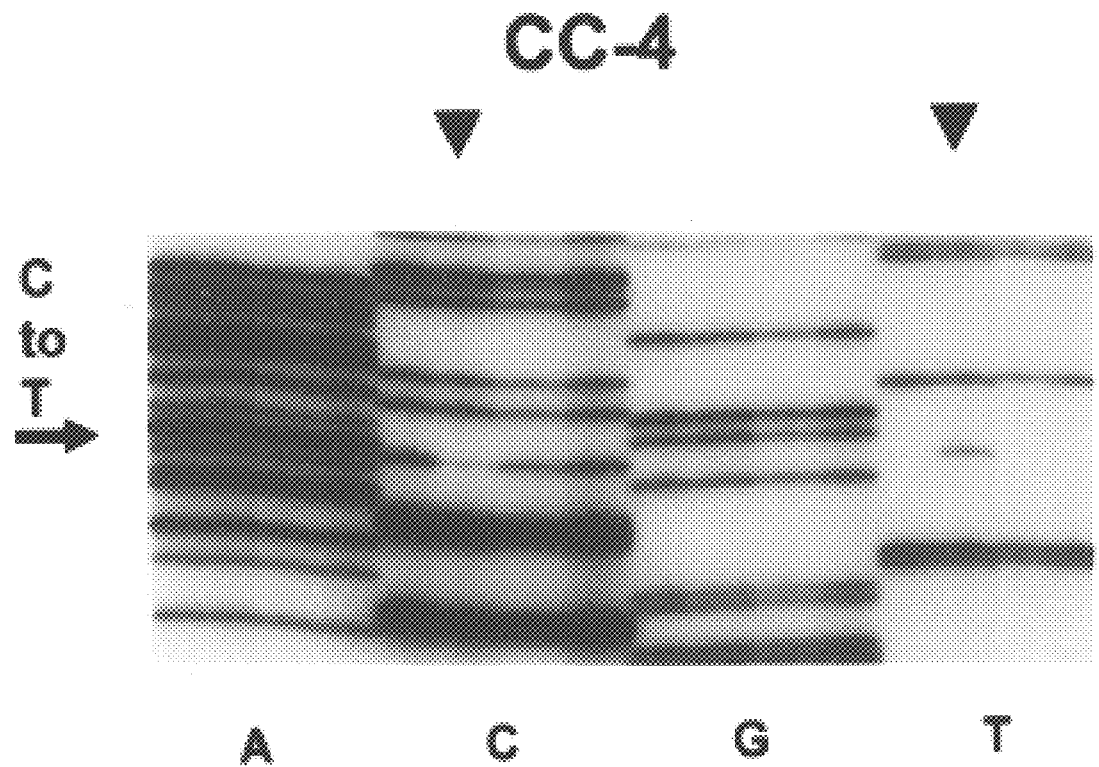
FIG. 7 shows DPC4 mutation in a sequencing gel for exon 11. The high grade dysplasia in patient CC-4 has a C to T nucleotide substitution, producing a new band in the T lane and a reduction of intensity in the C lane (arrows). A residual signal in the C lane is from the nonneoplastic stromal and inflammatory cells of the tumor, which contain the wild-type sequence. Lanes for each nucleotide are arranged by groups of four samples to improve pattern recognition.

An example of the sequencing results is shown in FIG. 7. FIG. 7 shows DPC4 mutation detections in a sequencing gel for exon 11. The high grade dysplasia in patient CC-4 has a C to T nucleotide substitution, producing a new band in the T lane and a reduction of intensity in the C lane (arrows). A residual signal in the C lane is from the nonneoplastic stromal and inflammatory cells of the tumor, which contain the wild-type sequence. Lanes for each nucleotide are arranged by groups of four samples to improve pattern recognition.

DCP4 sequencing results were combined with previous data to provide updated molecular genetic profiles for these lesions (Table 5). Patient CC-4 had a high-grade dysplasia containing a nonsense mutation of DPC4 at codons 516, which changes a glutamine codon (CAG) to a stop codon (TAG). Specimen CC-4 was one of three lesions in this study known to have allelic loss of 18q. No silent mutations, frameshift mutations, splice site mutations, or polymorphic, or polymorphic variants of DPC4 were identified.

TABLE 5

DPC4 Status and Molecular Genetic Profiles of Colitis-Associated Neoplasms

| Sample | K-ras[a] | APC[a] | 5q Loss | p53[a] | 17p Loss | DPC4[a] | 18q Loss | FAL | RER |
|---|---|---|---|---|---|---|---|---|---|
| CC-1 | wild-type | — | LOH | 282 R⇒W | LOH | — | LOH | 0.43 | — |
| CC-2a | 12 G⇒D | — | — | 195 I⇒I | LOH | — | — | 0.15 | — |
| CC-3 | 12 G⇒D | — | — | 179 H⇒Y | LOH | — | LOH | 0.29 | — |
| CC-4 | wild-type | 1450 R⇒stop | 1556 fs ins | 278 fs del | LOH | 516 Q⇒Stop | LOH | 0.22 | — |
| CC-5a | 12G⇒D | 1534 fs del | LOH | 262 splice | LOH | — | ND | 0.16 | — |
| CC-6a | wild-type | — | — | 248 R⇒Q, 282 R⇒W | — | — | — | 0.00 | RER[+] |
| CC-6b | wild-type | — | — | 282 R⇒W | — | — | — | 0.00 | RER[+] |

"LOH", LOH found; "RER[+]" multiple allelic shifts indicative of RER[+] phenotype; "–", no LOH, mutations, or allelic shifts detected; ND, not determined, [a]K-ras, p53, and DPC4 mutations are given by codon and the predicted translation product using the single letter amino acid code. fs del, frameshift deletion mutation; fs ins, frameshift insertion; splice, splice acceptor site mutated. For APC, mutations were identified by a screening assay, and the failure to identify a mutation does not exclude the possibility of certain types of sequence mutations. For DPC4, the tendency of this gene to be homozygously deleted makes negative sequence data an ambiguous finding. CC-4 had two mutations in APC. CC-6a had a p53 missense mutation on each allele. For each assay, non-dysplastic mucosa in each case was tested and found to have had no abnormalities.

Although the invention has been described with reference to the presently preferred embodiment, it should be understood that various modifications can be made without departing from the spirit of the invention. Accordingly, the invention is limited only by the following claims.

We claim:

1. An antibody which specifically binds to the polypeptide of SEQ ID NO:2 or which specificfally binds with immunoteactive fragments of SEQ ID NO:2.

2. The antibody of claim 1, wherein the antibody is polyclonal.

3. The antibody of claim 1, wherein the antibody is monoclonal.

4. A method for detecting a cell proliferative disorder associated with DPC4 in a subject, comprising contacting a target cellular component containing DPC4 with an antibody that specifically binds to DPC4 polypeptide and detecting DPC4.

5. The method of claim 4, wherein the antibody is polyclonal.

6. The method of claim 4, wherein the antibody is monoclonal.

7. The method of claim 4, wherein the antibody is detectably labeled.

8. A diagnostic kit useful for the detection of a target cellular component indicative of a cell proliferative disorder associated with DPC4 comprising carrier means being compartmentalized to receive in close confinement therein one or more containers comprising a first container containing an antibody specific for DPC4.

9. The kit of claim 8, wherein the antibody is detectably labeled.

* * * * *